US011166543B2

(12) United States Patent
Serval et al.

(10) Patent No.: US 11,166,543 B2
(45) Date of Patent: Nov. 9, 2021

(54) ORAL HYGIENE SYSTEMS AND METHODS

(71) Applicant: Colgate-Palmolive Company, New York, NY (US)

(72) Inventors: Thomas Serval, Neuilly-sur-Seine (FR); Yann Nicolas, Neuilly-sur-Seine (FR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/841,845

(22) Filed: Apr. 7, 2020

(65) Prior Publication Data

US 2020/0229585 A1    Jul. 23, 2020

Related U.S. Application Data

(63) Continuation of application No. 16/218,044, filed on Dec. 12, 2018, now Pat. No. 10,646,029.

(Continued)

(51) Int. Cl.
| *A46B 15/00* | (2006.01) |
| *A61B 5/00* | (2006.01) |
| *A61C 17/22* | (2006.01) |
| *G09B 19/00* | (2006.01) |
| *A46B 9/04* | (2006.01) |
| *G09B 23/28* | (2006.01) |

(52) U.S. Cl.
CPC ...... *A46B 15/0006* (2013.01); *A46B 15/0008* (2013.01); *A46B 15/0012* (2013.01); *A61B 5/486* (2013.01); *A61C 17/225* (2013.01); *G09B 19/0084* (2013.01); *A46B 9/04* (2013.01); *A46B 2200/1066* (2013.01); *G09B 23/283* (2013.01)

(58) Field of Classification Search
CPC ............ A46B 15/0006; A46B 15/0008; A46B 15/0012; G09B 19/0084
See application file for complete search history.

(56) References Cited

U.S. PATENT DOCUMENTS

| 8,137,109 B2 | 3/2012 | Riebe |
| 8,159,352 B2 | 4/2012 | Jimenez |

(Continued)

FOREIGN PATENT DOCUMENTS

| CN | 105411165 A | 3/2016 |
| CN | 206238734 U | 6/2017 |

(Continued)

OTHER PUBLICATIONS

International Search Report and Written Opinion of the International Searching Authority in International Application No. PCT/US2018/065219 dated Apr. 23, 2019.

*Primary Examiner* — Curtis B Odom

(57) ABSTRACT

A method for promoting compliance with an oral hygiene regimen includes displaying, on a display device, a representation of at least a portion of a set of teeth of a user. The method also includes overlaying an indicium on the representation such that the indicium is associated with a first section of the representation. Responsive to a determination, via at least one of one or more processors, that a head of an oral hygiene device is positioned directly adjacent to a first section of the set of teeth that corresponds to the first section of the representation for at least a predetermined amount of time, the indicium is removed from the display device.

20 Claims, 14 Drawing Sheets

Related U.S. Application Data

(60) Provisional application No. 62/611,105, filed on Dec. 28, 2017.

(56) References Cited

U.S. PATENT DOCUMENTS

| | | |
|---|---|---|
| 8,681,008 B2 | 3/2014 | Jimenez |
| 10,172,443 B2 | 1/2019 | Wang et al. |
| 2008/0109973 A1 | 5/2008 | Farrell et al. |
| 2009/0215015 A1 | 8/2009 | Chu |
| 2014/0065588 A1 | 3/2014 | Jacobson et al. |
| 2014/0157538 A1 | 6/2014 | Jimenez |
| 2015/0044629 A1* | 2/2015 | Wang ................. A46B 15/0006 433/27 |
| 2016/0027327 A1* | 1/2016 | Jacobson ................. G09B 5/06 434/263 |
| 2017/0069083 A1 | 3/2017 | Vetter et al. |
| 2019/0045916 A1* | 2/2019 | Jeanne ............... A46B 15/0006 |

FOREIGN PATENT DOCUMENTS

| | | |
|---|---|---|
| GB | 2519579 A | 4/2015 |
| RU | 2404696 | 11/2010 |
| RU | 2421116 | 6/2011 |

\* cited by examiner

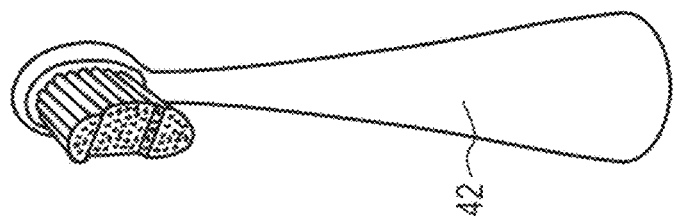
FIG. 3E
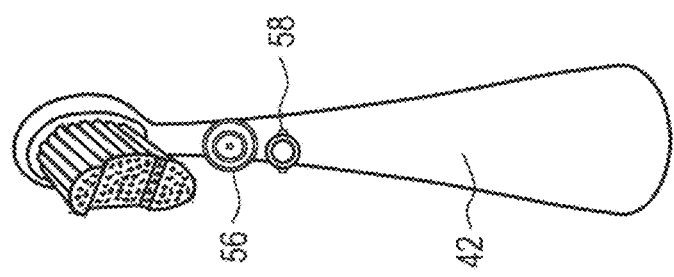
FIG. 3D
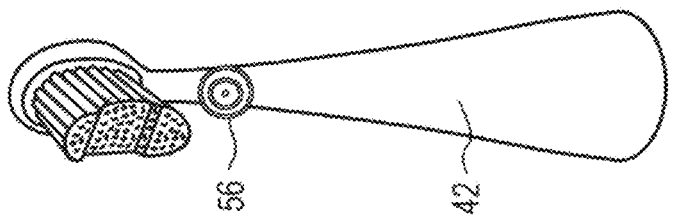
FIG. 3C
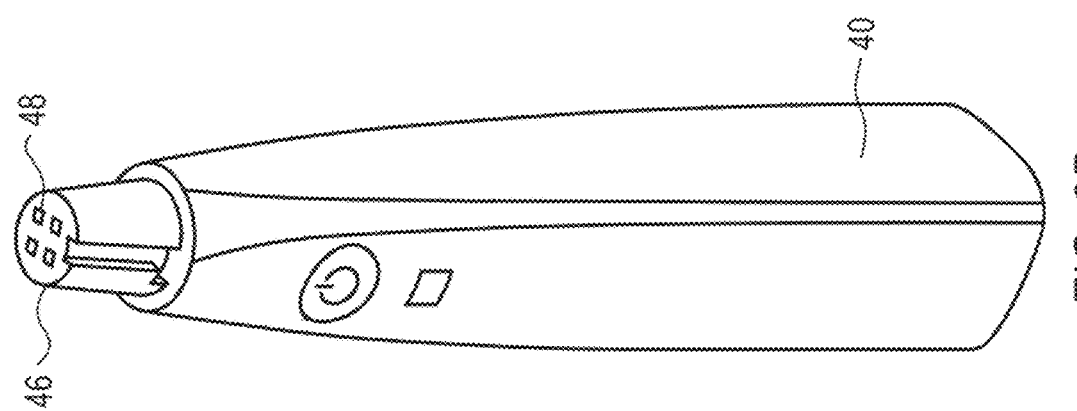
FIG. 3B
FIG. 3B-3E

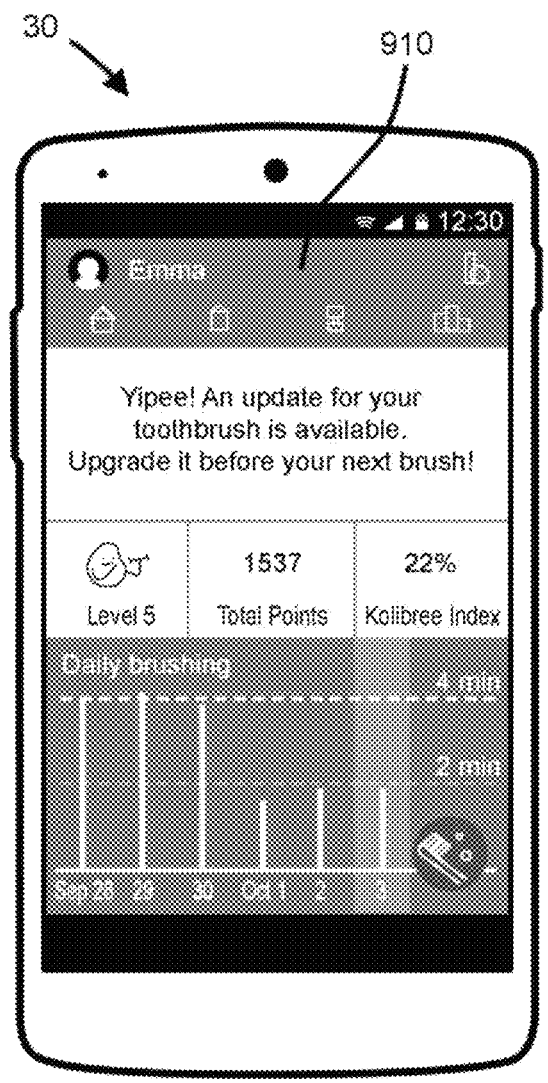 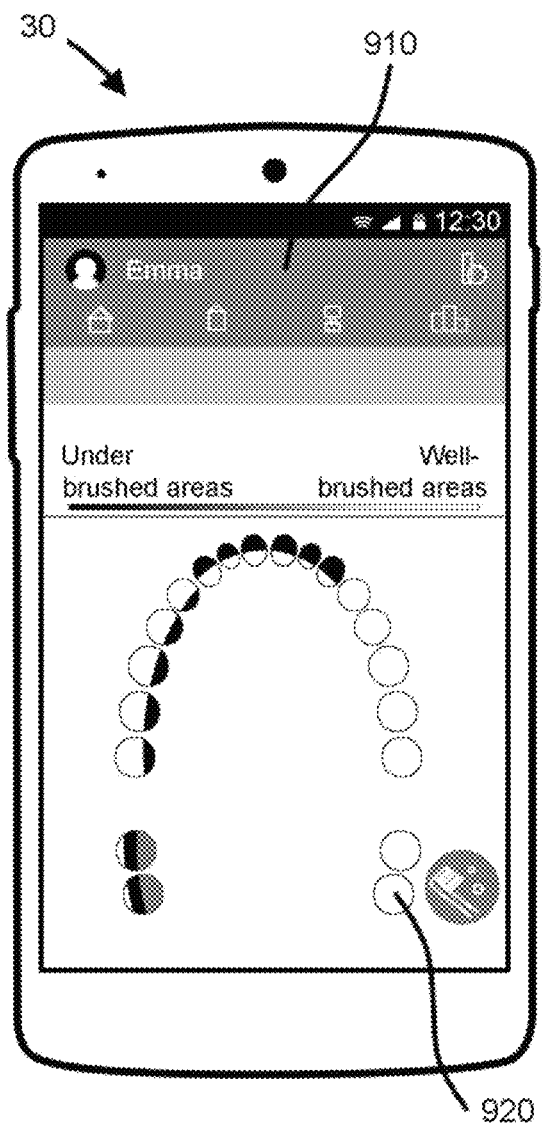
FIG. 9A     FIG. 9B
FIG. 9A-9B

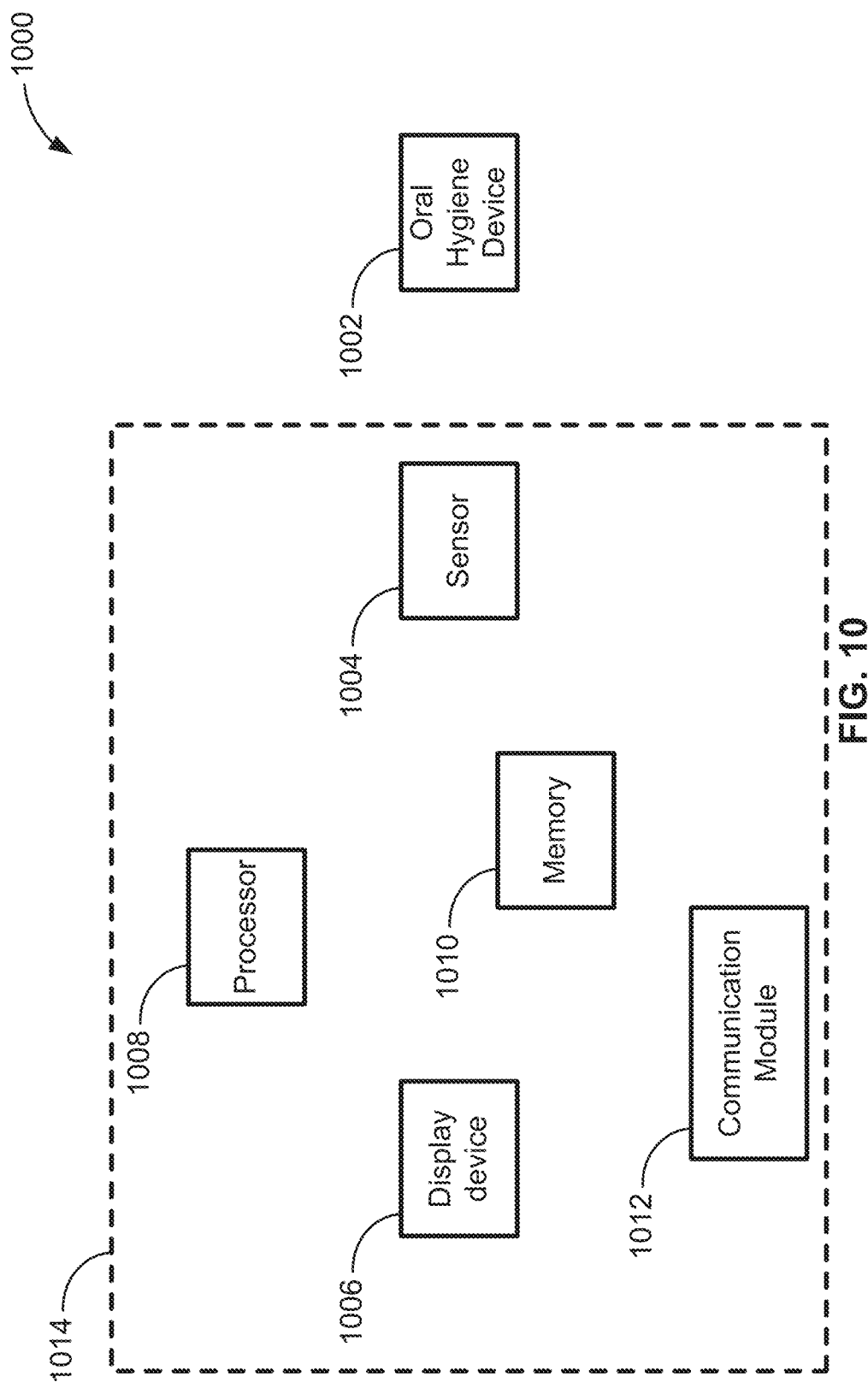

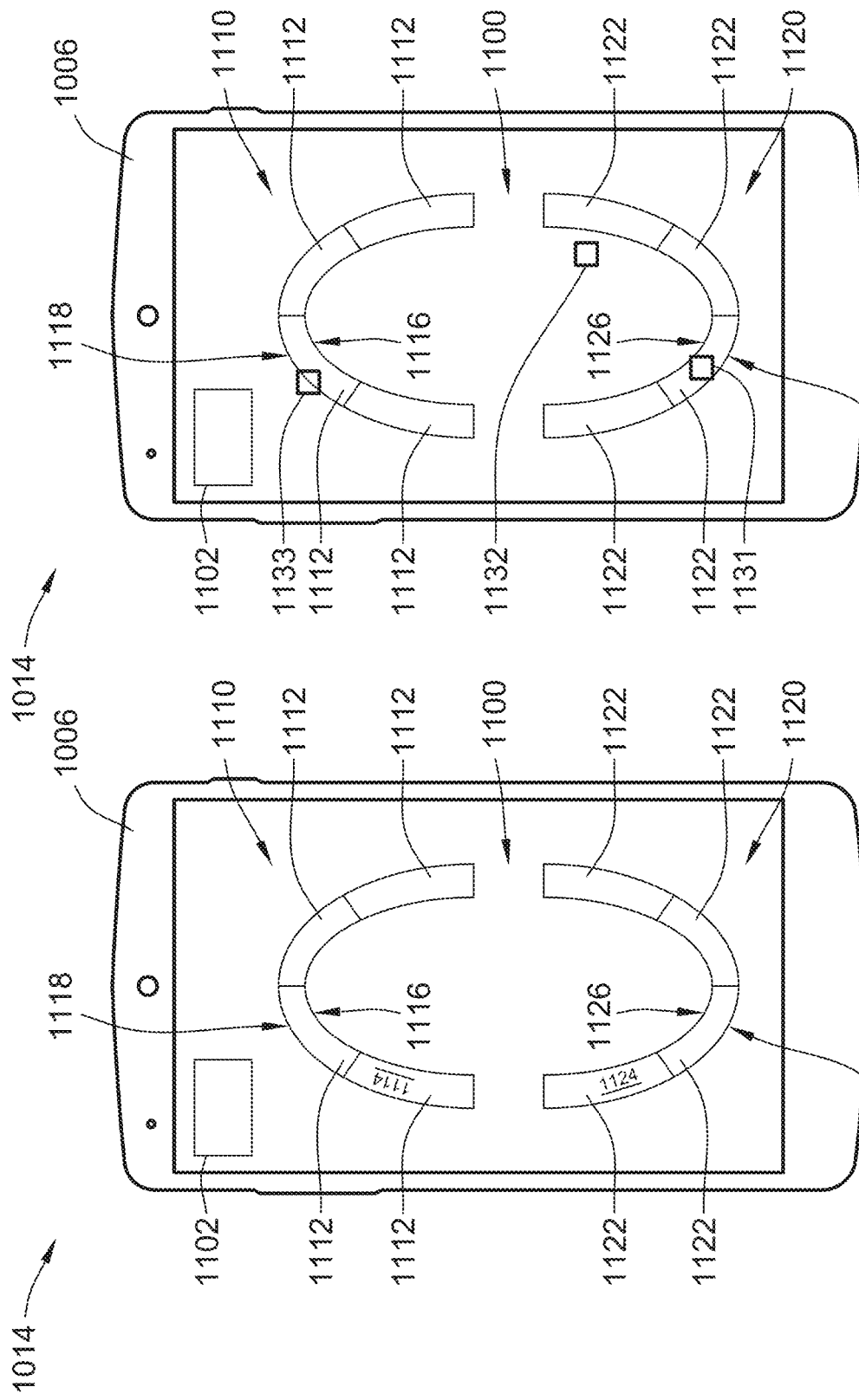

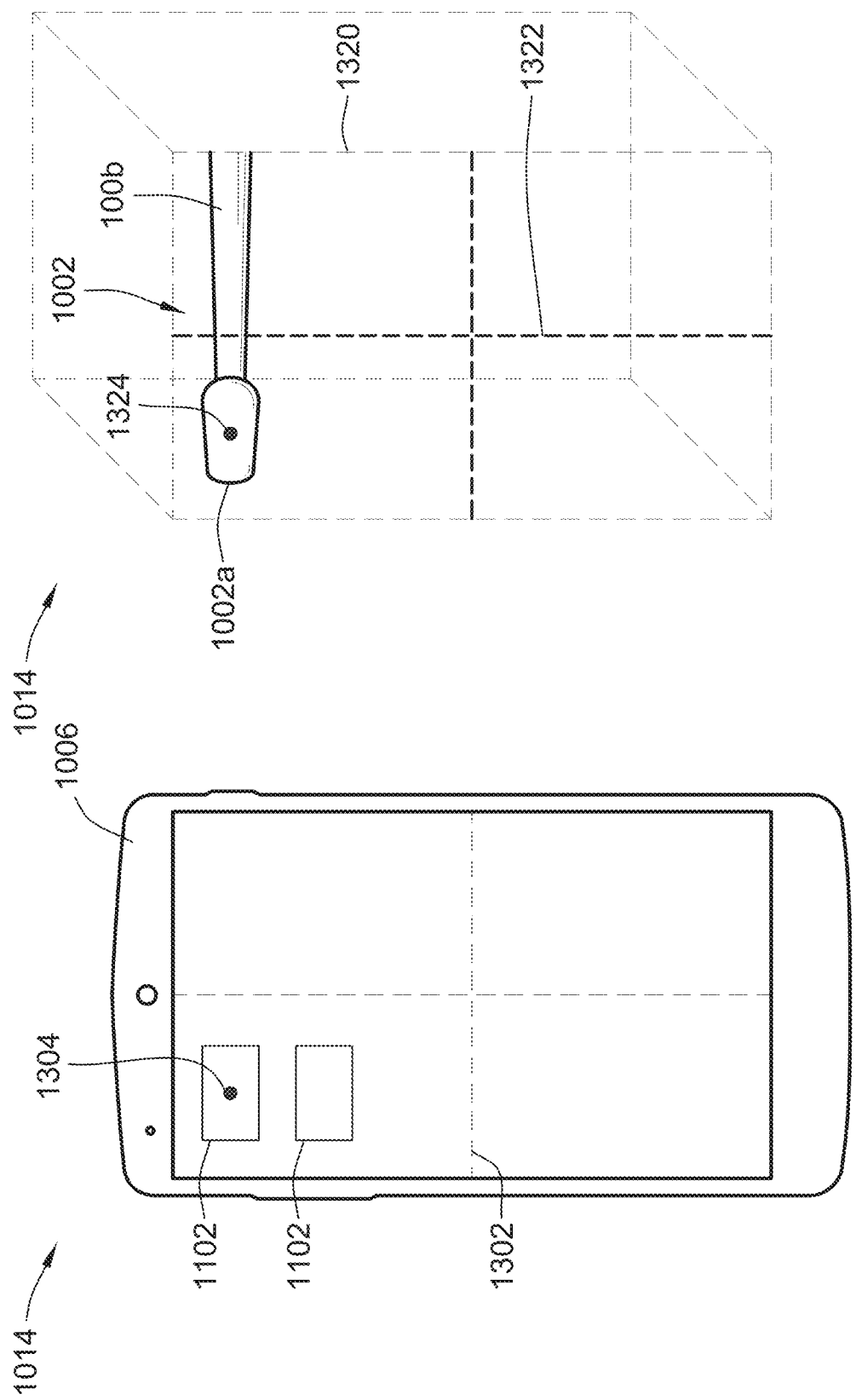

ORAL HYGIENE SYSTEMS AND METHODS

CROSS-REFERENCE TO RELATED APPLICATIONS

The present application is a continuation of U.S. patent application Ser. No. 16/218,044, filed Dec. 12, 2018, which in turn claims the benefit of U.S. Provisional Patent Application No. 62/611,105, filed on Dec. 28, 2017, the entireties of which are incorporated herein by reference.

FIELD OF THE PRESENT DISCLOSURE

The present disclosure relates generally to oral hygiene systems, and more particularly, to oral hygiene systems and method for promoting compliance with an oral hygiene regimen.

BACKGROUND

Compliance with proper technique and frequency of oral hygiene activities, including brushing and flossing, is essential for healthy teeth. Plaque, a bacterial biofilm, forms on teeth and contributes to tooth decay, gingivitis, and other dental problems. However, plaque can be removed by brushing at least once a day for two minutes, and preferably twice a day, inhibiting or mitigating tooth decay.

However, compliance with an oral hygiene regimen is especially poor among children and adolescents. For instance, many section of the teeth are frequently missed after bad habits develop. According to the CDC, although preventable, tooth decay is the most common chronic disease of children aged 6-11 (25%) and adolescents aged 12 to 19 years (59%). Also, 28% of adults aged 35 to 44 have untreated tooth decay. Research shows that children continually miss the same areas during brushing which leads to isolated buildups of plaque on certain teeth. Accordingly, more important than the length of time of brushing, is the efficacy of the tooth brushing. Additionally, dental health education only has been shown to generally only have a small and temporal effect on plaque accumulation. According to the American Dental Association, the compliance with proper oral hygiene regimens is quite low. For instance, only 49% of men and 57% of women brush their teeth twice a day.

Accordingly, there is a need for oral hygiene systems and methods that promote a user's compliance with dentist recommended hygiene regimens to decrease cavities, gum disease, and other dental complications from lack of brushing. The present disclosure is directed towards addressing these needs and other problems.

SUMMARY OF THE PRESENT DISCLOSURE

According to some implementations of the present disclosure, a method for promoting compliance with an oral hygiene regimen includes displaying, on a display device, a representation of at least a portion of a set of teeth of a user. The method also includes overlaying an indicium on the representation such that the indicium is associated with a first section of the representation. Responsive to a determination, via at least one of one or more processors, that a head of an oral hygiene device is positioned directly adjacent to a first section of the set of teeth that corresponds to the first section of the representation for at least a predetermined amount of time, the indicium is removed from the display device.

According to some implementations of the present disclosure, an oral hygiene system includes an oral hygiene device, a sensor, a display device, one or more processors, and a memory device. The oral hygiene device includes a handle and ahead. The memory device stores instructions that, when executed by at least one of the one or more processors, cause the oral hygiene system display, on the display device, a representation of at least a portion of a set of teeth of a user. The instructions also cause the oral hygiene system to overlay an indicium on the representation such that the indicium is associated with a first section of the representation. Responsive to a determination, via at least one of the one or more processors, that the head of the oral hygiene device is positioned directly adjacent to a first section of the set of teeth that corresponds to the first section of the representation for at least a predetermined amount of time, the indicium is removed from the display.

According to other implementations of the present disclosure, a method for promoting compliance with an oral hygiene regimen includes displaying, on a display device, a representation of at least a portion of a set of teeth of a user. The method also includes overlaying an indicium on the representation such that the indicium is associated with a first section of the representation. Responsive to a determination, via at least one of one or more processors, that a head of an oral hygiene device is positioned directly adjacent to a first section of the set of teeth that corresponds to the first section of the representation for at least a period of time, the indicium is removed from the display device. The indicium is one of a still image, a video image, or an animated image.

In yet another implementation of the present disclosure, an oral hygiene system includes an oral hygiene device, a sensor, a display device, one or more processors, and a memory device. The oral hygiene device includes a handle and ahead. The memory device stores instructions that, when executed by at least one of the one or more processors, cause the oral hygiene system display, on the display device, a representation of at least a portion of a set of teeth of a user. The instructions also cause the oral hygiene system to overlay an indicium on the representation such that the indicium is associated with a first section of the representation. Responsive to a determination, via at least one of the one or more processors, that the head of the oral hygiene device is positioned directly adjacent to a first section of the set of teeth that corresponds to the first section of the representation for at least a period of time, the indicium is removed from the display. The indicium is a graphic symbol representing an object.

BRIEF DESCRIPTION OF THE DRAWINGS

FIG. 3B is a perspective view of an example of an oral hygiene device handle;

FIGS. 3C-3E are perspective views of an example replaceable heads that may be attached to a head interface;

FIG. 9A is a front view illustrating an example of a mobile device display with brushing feedback;

FIG. 9B is a front view illustrating an example of a mobile device display with brushing feedback;

FIG. 10 is a schematic illustration of an oral hygiene system according to some implementations of the present disclosure;

FIG. 11A is a front view of a display device of the oral hygiene system of FIG. 10;

FIG. 11B is another front view of a display device of the oral hygiene system of FIG. 10;

FIG. 13A is a front view of a display device of an oral hygiene system according to some implementations of the present disclosure; and FIG. 13B is a front view of an oral hygiene device in a three-dimensional volumetric space.

DETAILED DESCRIPTION

Figure 1:
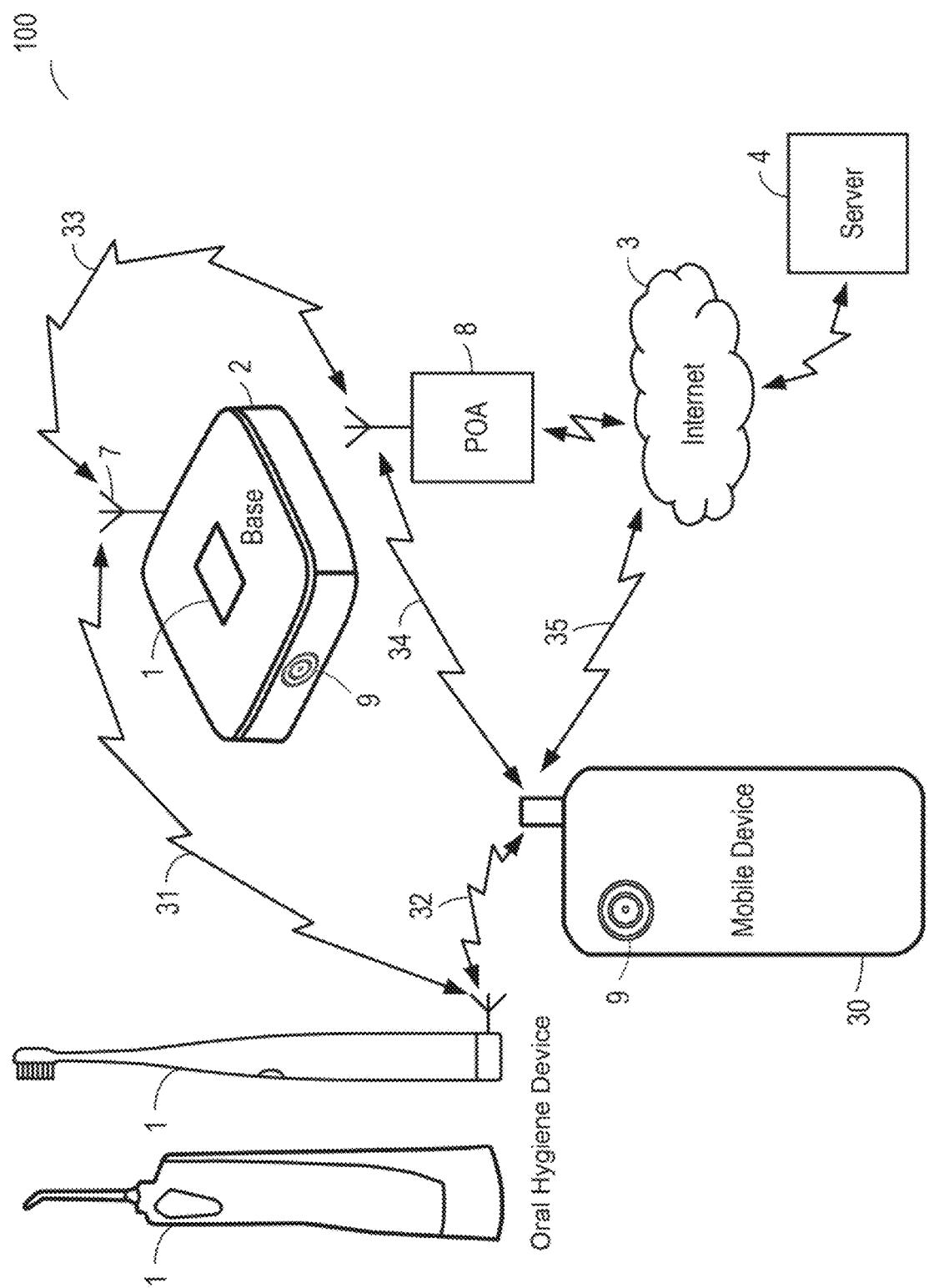
FIG. 1 is a schematic view of an example of an oral hygiene system.

FIG. 1 illustrates an overview of an oral hygiene device monitoring and feedback system 100 that includes: an oral hygiene device 1 equipped with sensors, a base station 2 for receiving and charging the oral hygiene device 1, a mobile device 30 that wirelessly receives/sends data, a dedicated wireless link POA 8, a server 4 and a network 3 for transferring the information from the server or between other various components of the system 100.

Data Communication

The oral hygiene device 1 may have an antenna 5 and transceiver means for radio communication to a compatible complementary antenna 5 and transceiver means of the base station 2 through a radio link 31. The radio-communication link 31 may be for example WiFi or GSM or Bluetooth or their derivatives or other proprietary protocols. Additionally, one or more optical sensors 9 may communicate with a mobile phone 30, base station 2, server 4, or other associated computing device as disclosed herein.

In another embodiment, antennas and transceiver means are replaced or completed by wired connections or connectors to allow the exchange of information between the oral hygiene device 1, optical sensor/camera 9, and/or the base station 2. Wired connectors may also provide electric power supply from the base station to the oral hygiene device 1 for recharging a rechargeable electric source of the latter. In another embodiment, the electric power supply from the base station to the oral hygiene device 1 or optical sensor device 9 is provided with electromagnetic induction circuitry.

The base station 2 may be powered through a power cord. The base station 2 may alternatively be powered by a rechargeable battery which is charged from time to time with a battery charger powered by the power supply grid. The base station 2 has a receiving slot for physically supporting and storing the tooth brush when it is not used by a user.

The base station 2 and or separate optical sensor device 9 includes a data exchange circuit, for communicating data with a network 3, for example the internet. Data may be transferred using a radio-communication link 31, as illustrated in FIG. 1, with the antenna 5 of the base station 2 and with the antenna 5 of a dedicated communication equipment 8 or POA, connected to the network 3. In other embodiments, transfer of data between the base station 2 and the network 3 are performed through a wired link, for example ADSL.

The antenna 5 and transceiver means of the oral hygiene device 1 and/or camera/optical sensing device 9 is also compatible with radio communication means of a mobile device 30 over a radio link 31. The radio-communication link 31 is for example WiFi or GSM or Bluetooth or their derivatives or other suitable protocols. In some embodiments, radio links 31 are short range, local, radio communication links or a radio link 35 such as the ones used in cellular or other mobile phone systems (GSM and derivatives for example).

The mobile device 30 is also able, via its radio communication circuits, to exchange data on a radio link 31 through the dedicated communication equipment 8 or POA, on the network 3. In addition, or alternatively, the mobile device 30 is able to exchange data on a radio link 35 directly on the network 3.

A server 4 is connected to the network 3 by any suitable means. Server 4 is defined broadly to include computing devices capable of storing and computational operations for example on the "cloud" in a computing network. The server 4 may include storage devices, for instance memory, hard disk drives, flash memory, or other storage devices and includes computational means under the control of a program. For the transfer of data, the oral hygiene device controlling circuit uses a predetermined server 4 address of the network 3. This predetermined address may be stored initially in the oral hygiene device 1 and/or updated later through the network 3. The transfer of data between the oral hygiene device 1 and server 4 may be performed: a) each time the oral hygiene device 1 is replaced in the base station 2 in a batch configuration, b) at the direction of the user or the server 4, for example by user action initiating the transfer using the interface of the mobile device 30 or a web page accessing the server 4 or c) in real time when oral hygiene device 1 activities are detected, or d) the oral hygiene device 1 is removed from the base station 2 or e) at other suitable intervals.

System Circuit Design and Network Architecture

Figure 2:
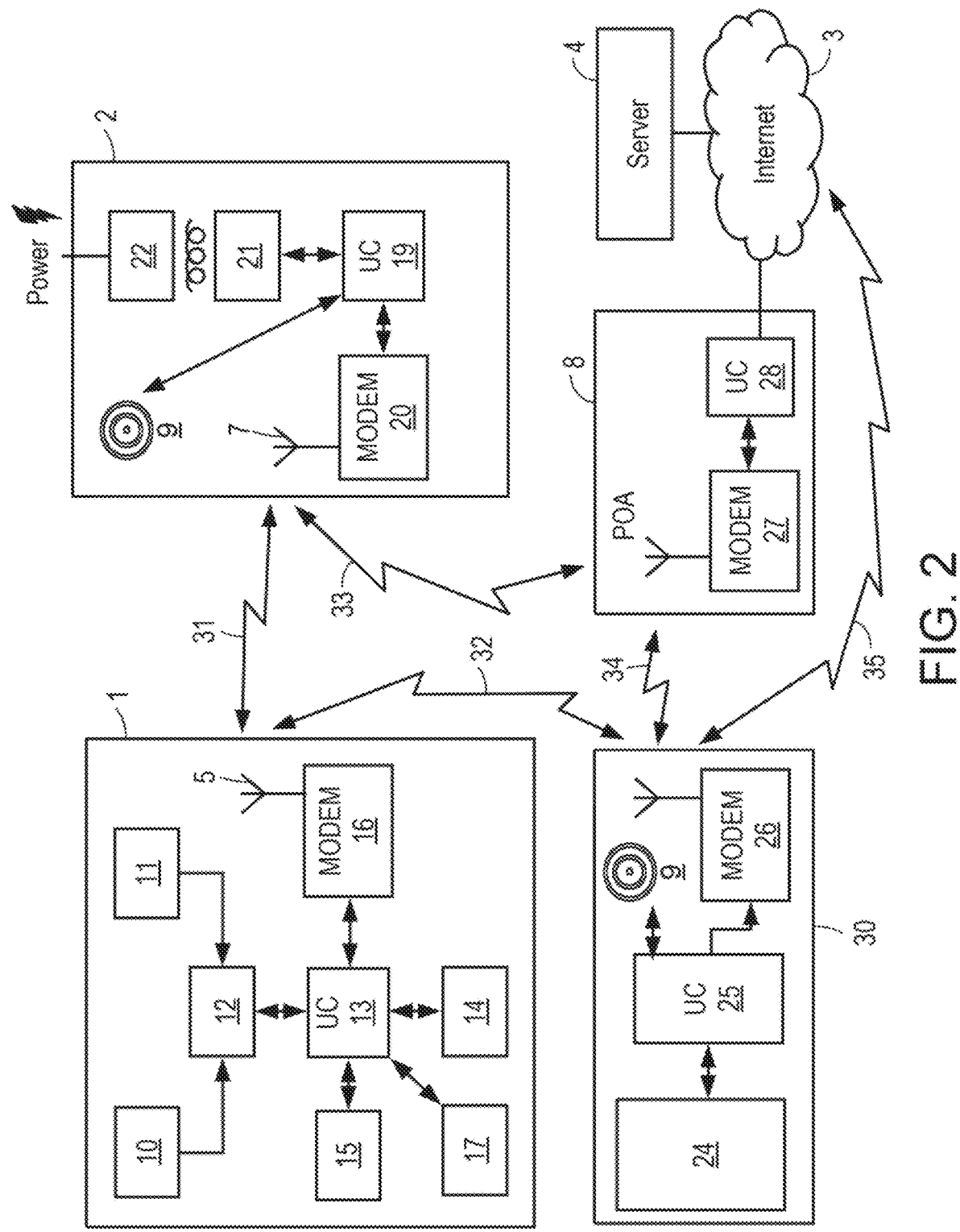
FIG. 2 is a diagrammatic view of an example of the oral hygiene device and of an example base station of the system of FIG. 1.

As illustrated in FIG. 2, the oral hygiene device 1 may include a pressure sensor 10 and at least one sensor 11. The sensor 11 shown in FIG. 2 can refer to any suitable type of sensor. The pressure sensor 10 detects force applied on the brushing side of the oral hygiene device 1 when a user applies the bristles to their teeth. The sensor 11 can be a motion sensor for detecting motion on any or all three of the orthogonal axes of the oral hygiene device 1, or a motion sensor may be able to detect accelerations or other motion characteristics in all three axes. The signals output by the sensors are processed by a signal conditioning circuits 12. Examples of signal conditioning include: frequency and noise filtering, amplification, conversion, digital signal processing, and other techniques to optimize the detected signals for analysis.

On other embodiments, the oral hygiene device 1 may not include any electronics and may be a standard toothbrush. In those embodiments, a separate optical sensor/camera 9 may perform the tasks of tracking the motion of the oral hygiene device 1.

The processed signals or raw data from the sensors are then stored in memory 14 as determined by a control system 13 which may be a digital signal processor, microcontroller, or other processing component and which operations are controlled by a program 15. The memory 14 may be included in the oral hygiene device 1 or on a server 4 or other component of the system 100. A program 15 may be updated through an oral hygiene device 1 interfacing circuit 16, a modem for radio communication, and its antenna 5 (and/or connector in case of contact/wired interface) or other interfaces of the oral hygiene device 1. More generally, the oral hygiene device interfacing circuit 16 allows information exchanges between the oral hygiene device 1, the optical sensor device 9, and the base station 2 when the radio link 31 is established (and/or connectors of the tooth brush and of the base station are mated together). The oral hygiene device 1 may contain a power supply circuit for powering the sensors and the circuits of the oral hygiene device 1 and it can include a rechargeable electric source 17.

The base station 2 may include a base station interfacing circuit 20, a modem for radio communication, with an antenna 5 (and/or connector) to exchange information over link 31. In addition, the base station interfacing circuit 20 is able to establish a radio link 31 with the dedicated communication equipment 8, for communication with the network 3. The base station 2 may utilize a power supply converter 22 which is regulated 21 to provide appropriate voltage and current to the base station circuits. Electrical connections (not illustrated) for providing charging current to the oral hygiene device 1 from the base station 2 may be provided. In some embodiments, the base station 2 may include a recharging circuit for recharging a battery or power supply of the toothbrush, through inductive charging or a direct electrical connection.

The base station 2, optical sensing device 9, or other separate electronic device may also include a magnetic field transmitter 110 that emits a magnetic field that may be sensed by an associated magnetometer or other magnetic field sensor. The magnetic field transmitter 110 may be provided by utilizing the charging circuits or other circuits that already exist in the base station 2 or other electronic device. For example, the base station 2 may have a recharging coil that could also serve as a magnetic field transmitter 110. The recharging coil may be fixed and in a known orientation, so as to create a magnetic field of known strength and polarity orientation. In some embodiments, the base station 2 may include a recharging coil that generates a magnetic field with a polar axis situated in a horizontal or vertical plane. In some embodiments, this may be a single axis magnetic field transmitter 110, such as in the case of a single axis recharging coil. In other embodiments, 2 or 3 axis magnetic field transmitters 110 may be incorporated into the base station 2. This will advantageously allow for a fixed magnetic field(s) of known orientation so that a magnetometer (sensor 11) on the oral hygiene device 1 may sense the strength and polarity of the magnetic field(s) in order to provide information regarding the position and orientation of the oral hygiene device 1, or the relative changes in position and orientation.

In some embodiments, the base station 2 or other electronic device separate from the oral hygiene device 1 may also include a camera 9 that may detect visual patterns on the oral hygiene device 1. The camera 9 may be any suitable camera that may detect a visual pattern on the oral hygiene device 1. For instance, the cameras provided with mobile phones would be suitable. In other embodiments, a stand-alone camera or optical sensing device 9, a separate camera stand for a mobile phone, a connected mirror or other camera or imaging device may be utilized.

In some embodiments, the base station 2 is passive and its circuits are under the control of the controller 13 of the oral hygiene device 1 when they are communicating together, specifically when the link 31 is of the wired/contact type with connectors. In the embodiment represented on FIG. 2, the base station has a control system 19 which controls its operations.

The dedicated communication equipment 8 may include a radio modem circuit 27 and the appropriate electronics for communicating with network 3. The dedicated communication equipment 8, is able to establish a radio link 31 with the base station 2 and/or a radio link 31 with the mobile device.

The mobile device 30 includes at least a radio modem 26 for establishing a radio link 31. The operations of the mobile device 30 are under the control of a control system 25, for instance, a central processing unit or μC, and of a program 15. The mobile device 30 includes an output means such as a display screen and an input means such as a virtual or material keyboard. Preferably, the input and output means of the mobile device 30 are used in the system to input information and to display information, notably the results of computations performed by a server. The mobile device 30 may also include a camera 9 that is capable of detecting visual patterns supplied on the oral hygiene device for detection of movement.

The program of the computational means of the server 4 allows storage of signals received from the oral hygiene device 1. Additionally, the server 4 may analyze the data from the sensors to produce feedback and motivational data regarding the user's performance in brushing their teeth. These results may be accessible to the user on an internet page hosted by the server 4 or transferred to another webserver for hosting. In a different embodiment, the previous operations and computations are done fully or partially in the mobile device 30, the server 4 being used for general monitoring.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Oral Hygiene Device Design

Figure 3A:
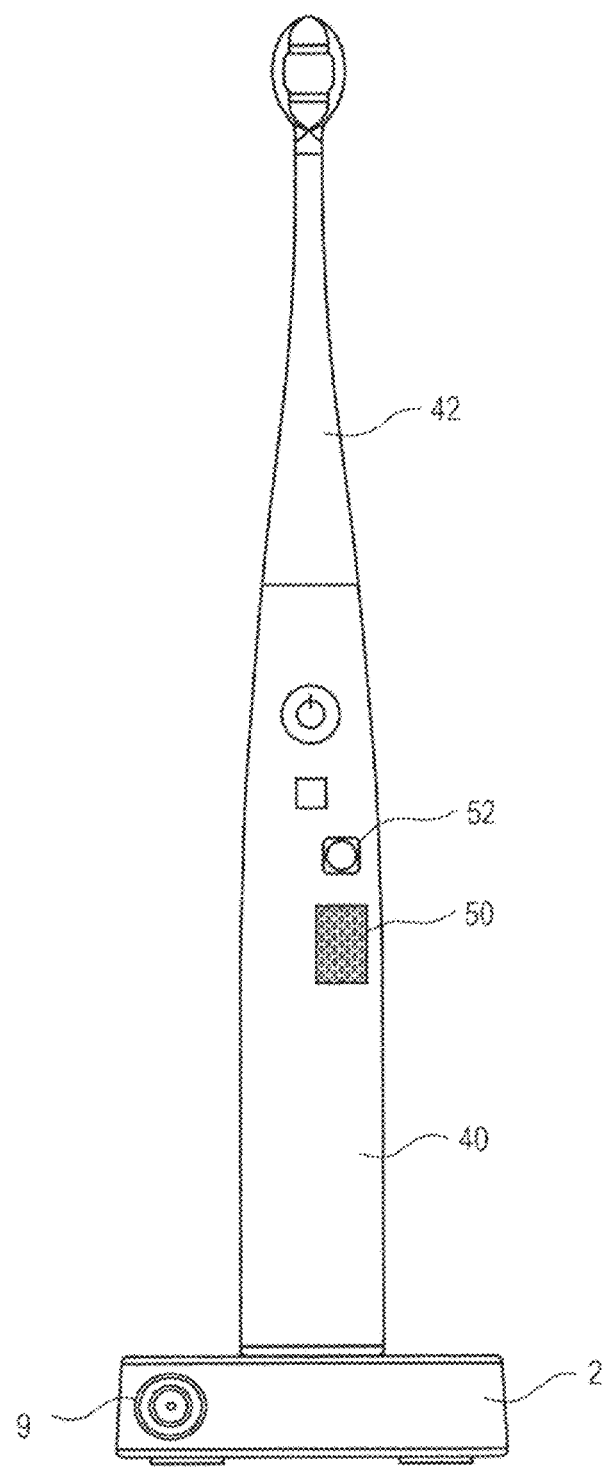
FIG. 3A is a perspective view of an oral hygiene device and head according to some implementations of the present disclosure.

As illustrated in FIGS. 3A-3C, the oral hygiene device oral hygiene device 1 may include a handle 40, and a head 42 that may be removably connectable to the handle 40. The handle 40 may contain a motor that is mechanically connected to the head 42 and when activated vibrates or moves the head 42 in manner that brushes a user's teeth when placed inside the mouth. The handle 40 includes a head interface 46 that removably attaches various heads 42 to the handle 40. The head interface 40 contains leads 48 for both data and power transfer to various heads 42. For example, certain heads 42 may include sensors that require power and data transfer, and therefore power can be routed from the handle's 40 power source to the head 42 through leads 48 that form a connection with the head 42 at the head interface 46. The may be various numbers of leads 48 that form the connection on the head interface 46, for instance there may be two leads 48 for power, and two leads 48 for data, three leads 48 for power, three leads 48 for data, and other various numbers of leads. In some embodiments the head interface 46 will form a watertight seal with the head 42 to prevent water from entering the interface and interfering with the electrical leads 48 power and data transfer.

In some embodiments, the majority of the circuitry and costly components can be contained inside the handle 40 as opposed to the head 42, which may be disposable after a certain number of uses. This will minimize the cost of the replacement heads 42. For example, in some embodiments, the battery, controller 13 may be contained in the handle 40, and any sensor probes and circuitry to connect the sensor probes may be contained in the head 42. In other embodiments, the head 42 may contain no circuitry or electrical components and will only provide a mechanical brushing function by supporting the bristles.

Figures 8A, 8B, 8C:
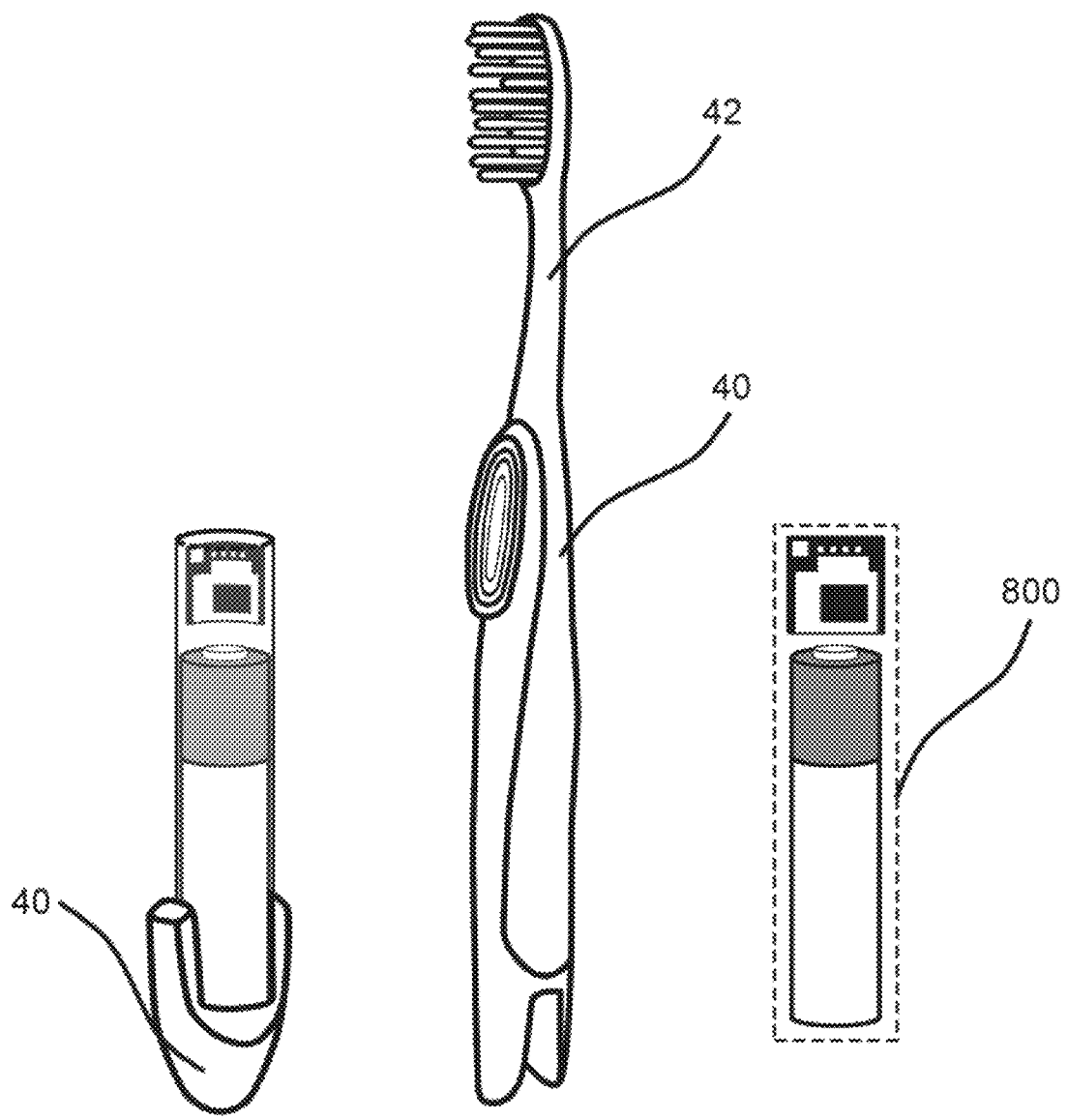
FIG. 8A is a perspective view illustrating an example of a toothbrush handle with an insert.
FIG. 8B is a perspective view illustrating an example of a toothbrush with an insert removed.
FIG. 8C is a perspective view illustrating an example of an insert that includes a battery and electronics for a toothbrush.

For instance, as illustrated in FIGS. 8A-8C, the electronics and battery may be contained inside an insert 800 that is easily slidable into a conventional oral hygiene device 1. For instance, an oral hygiene device 1 may include a chamber and connector that is connectable to a base and insert 800 that slide into the chamber and the base forms a watertight seal with the connector. The insert 800 could be any manner of shapes (cylindrical, rectangular or others) that would slide inside a space of the toothbrush. In some examples, the base and connector will contain a screw and thread mechanism to attach the toothbrush. In some examples, the connector and base will include a press-fit mating configuration for easy connection and detachment. For instance, the connection may be made with opposing wings on the connector and the base as illustrated in FIGS. 8A-8C.

In some embodiments, oral hygiene device 1 may only be a standard toothbrush, or other standard oral hygiene device 1 that is commercially available and may not have electronics, or may only have electronics for moving the head to facilitate brushing. In some embodiments, the oral hygiene device 1 may only include patterns 120 or an attachment 130 with a pattern 120, and may not include any motion sensing electronics, or may not include any electronics at all. Accordingly, in these embodiments, the visual tracking software may be utilized to determine position and orientation of the oral hygiene device 1.

The oral hygiene device 1 may also include a speaker 50 and various visual indicators 52 to provide audio and visual feedback to the user. For example, the handle 40 may contain a speaker 50 for playing music, substantive feedback, motivational phrases, remaining time elapsed, recommendations on brushing pressure, on whether certain quadrants have not been adequately brushed, an announcement for completion of brushing, etc. Additionally, the oral hygiene device 1 may contain any number of visual indicators 52, for providing substantive feedback on the brushing including time elapsed, a LED indicator for when brushing is complete, warning indicators for brushing inappropriately, including indicators for whether each quadrant has been addressed. In other embodiments, the oral hygiene device 1 may also utilize osteophony to convey audio messages to the user.

Figure 6A:
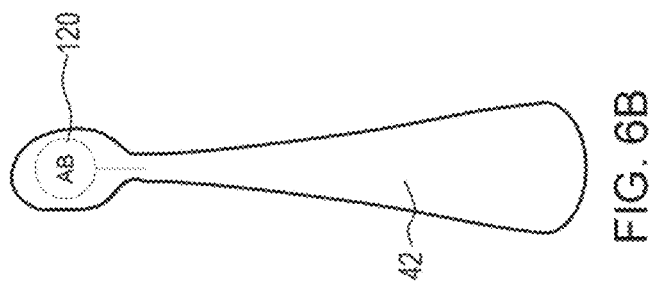
FIG. 6A is a perspective view illustrating an example of an oral hygiene device with visual patterns according to some implementations of the present disclosure.
Figure 6B:
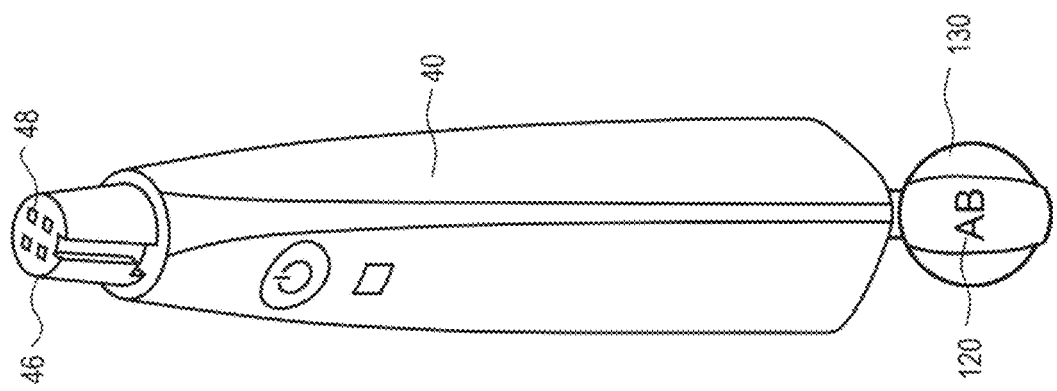
FIG. 6B is a perspective view illustrating an example of an oral hygiene device head with visual patterns according to some implementations of the present disclosure.

As illustrated in FIG. 6, the oral hygiene device 1 may contain a handle 40 and head 42, where either or both may include a pattern 120 for visual detection of movement and orientation by an associated camera 9. For instance, in some embodiments, the back of the head 42 may contain a pattern (i.e. "AB" with a circle and line as illustrated). In other embodiments, the pattern 120 may be contained on an attachment 130 that may be attachable to the head or on the neck, painted in the bristles, or other positions.

The handle 40 may also include a pattern 120, or in some embodiments may be the only component that includes a pattern 120. The pattern 120 on the handle 40 may be applied directly to the handle 40 or may be in an attachment 130 that clips or connects to the end of the handle 40. The pattern 120 may be positioned at a convenient location on the attachment 130 or on the handle 40 so that it may be detected in all angles of normal brushing activity. In some embodiments, the handle 40 may include multiple patterns 120 on different sides for detecting different orientations. For instance, in some embodiments, the attachment 130 may be square or circular and have a different pattern 120 on each side in order for the system to detect the orientation of the oral hygiene device with respect to the camera.

The attachment 130 may be weighted so that the oral hygiene device 1 stands by itself when set on a flat surface. For instance, a weight that is heavy enough 130 to keep the oral hygiene device 1 upright may be applied to the bottom of the attachment 130. In some embodiments, this may be particularly useful if the attachment 130 is spherical on the bottom. This will give the oral hygiene device an entertaining quality that will be intriguing to children and even adults.

Pattern 120 may be applied using paint, other marking processes, or it may use reflective coatings, mirrors, or fluorescent coatings. In some embodiments, pattern 120 may utilize color, or it may be grayscale.

Oral Hygiene Device without Pattern or Electronics

A standard oral hygiene device 1 or oral hygiene device may be utilized without any electronics or patterns. As indicated, in some embodiments the position and motion of the oral hygiene device 1 will be detected.

Sensors

The oral hygiene device 1 or separate electronic devices (e.g. optical sensors) may incorporate various sensors that detect certain attributes of brushing that may be analyzed to provide various feedback and other motivational information to the user. For instance, one or more optical sensors 9 may also be utilized on a separate electronic device to detect an orientation and movement of the oral hygiene device 1. For instance, the optical sensors 9 may be utilized to capture images of an oral hygiene device 1, and the images may be sent for processing to identify its borders, shape, longitudinal axis, and orientation (for example by identifying its bristles). In some embodiments, the optical sensor(s) 9 may be utilized may detect patterns on the oral hygiene device 1 rather than the oral hygiene device 1 itself. The optical sensor(s) 9 utilized for pattern detection may be oriented in a direction to provide a visual line of sight to the pattern 120 on the oral hygiene device 1 that may be on the head 42, handle 40 or on an attachment 130.

As another example, the oral hygiene device 1 may incorporate various motion sensors 11 to determine the quality of the brushing with respect to certain quadrants of the mouth or even individual teeth. The motion sensors 11 may include gyroscopes, accelerometers, magnetometers, gyrometers, and other various sensors capable of detecting positions, movement, and acceleration. These various motion sensors 11 may be incorporated either in the handle 40 or the head 42. However, it may be advantageous to put the motion sensor 11 in the handle 40 because in some embodiments where the motion sensor 11 is in the head 42, the motion sensor 11 can experience at lot of additional motion (e.g., due to brushing and engagement with teeth) that may interfere with detecting a position. In some embodiments, a magnetometer will sense a vector(s) of the earth's magnetic field. In some embodiments, a three-axis magnetometer will be used and in others a two or one axis magnetometer will be utilized.

A magnetic field generator 110 may also be utilized to generate a known magnetic field with a known polarity that may be sensed by a magnetometer incorporated into the oral hygiene device 1. The magnetic field transmitter 110 may be placed inside the base station 2 which would already have a recharging coil and/or interfacing circuit 20 that may be utilized to produce a detectable magnetic field. In other embodiments, the magnetic field transmitter 110 may be a separate electronic component in the base station 2 or in a separate physical component entirely. In some embodiments, the magnetic field transmitter 110 would be in a stationary unit with a known orientation.

The oral hygiene device 1 may also incorporate various proximity sensors that detect the proximity of the oral hygiene device 1 to the mouth of a user. These may be incorporated at the head 42 or in the handle 40. The proximity sensors may be utilized to acquire additional positional information relevant to determining the brushing quality of the user.

Additionally, the oral hygiene device 1 may contain a pressure sensor 10 to determine whether the user is applying appropriate pressure in brushing their teeth. The pressure sensor 10 may be incorporated into the head 42 which may be more easily flexible or utilize simple pressure transducers or other components capable of measuring pressure.

In certain examples, the oral hygiene device may contain a pH sensor 10. The pH sensor 10 may be utilized to determine the salivary pH of a user. For instance, in some examples, a user may be instructed to place the oral hygiene device 1 in the user's mouth prior to using toothpaste or mouthwash, to test the salivary pH. Salivary pH may be indicative of periodontal disease or gingivitis.

In other examples, the oral hygiene device 1 or system 100 may also include a depth perception sensor. For instance, in some examples the depth perception sensor will project a laser light grid or other laser pattern from the base station 2, for example in place of camera 9, and include a detector that will detect and analyze distortions in the pattern to determine depth. The depth perception sensor may be utilized to determine more accurately the outlines of separate objects for identification and motion tracking. For instance, the system 100 may be able to more easily identify the user's head and facial features, and distinguish from the oral hygiene device 1. Accordingly, the depth perception device may be utilized to determine movement in a plane parallel to the line connecting the base station 2 to the user.

In some examples, the oral hygiene device 1 may also contain a depth perception device. For instance, in some examples, the oral hygiene device 1 may include a depth perception projector and sensor that projects onto the user's teeth. This may be utilized to form a map of the user's teeth and to detect holes or cavities in the user's mouth.

In some embodiments, various heads 42 may incorporate a camera 56 that will detect various aspects of tooth quality that may or may not be related to brushing quality. For example, a camera 56 including a near infrared camera 56 may be able to be utilized on an oral hygiene device 1 to collect data indicative of demineralization or dental caries or dental decay. For example, the oral hygiene device 1 may utilize certain wavelengths that are particularly suited to detect these abnormalities, for instance in the 1300-1400 nm range. In some embodiments, the oral hygiene device 1 may also contain a light source 58 that will be focused towards the teeth during brushing and can be utilized by the camera to detect certain abnormalities.

In some examples, the output of the camera 56 may be utilized by the system 100 to form a tarter map of the user's mouth. For instance, in some examples, the system 100 may utilize the images from the camera 56 to identify tarter based on the reflection wavelengths, and build a schematic or other representation of the tarter for the user's mouth. For instance, the camera 56 may utilize certain wavelengths and/or filters that reflect tarter more readily, and identify which areas of the mouth have more or less areas of tarter, or other issues. For instance, tarter may cause light to reflect less, and may also reflect different wavelengths. These different patterns can be filtered or detected by machine learning algorithms by the system as described in further detail below.

Certain cameras 56 and potentially light sources 58 may also be implemented to detect levels of plaque on the teeth and changes in levels of plaque during brushing. In certain embodiments, infrared or near-infrared light sources 58 and an appropriate camera 56 that detects and records light in this wavelength range may potentially allow for the detection of plaques.

Program for Brushing Analysis and Feedback

The systems various sensors and optical sensors may gather data relevant to the quality of brushing by a user or the overall dental health of a user's teeth. This data may then be processed using programs or applications installed in various portions of the oral hygiene device monitoring system 100. Accordingly, as described above, data from the sensors and optical sensors may be processed by a program executed by the oral hygiene device's 1 control system 13 or alternatively a processor on the mobile device 30, another associated computing device, or the server's 4. The system's 100 processing and analysis of the data will result in output data representing feedback relevant to a user's quality of brushing. This feedback may be communicated through audio feedback through the oral hygiene device 1 speaker 50, visually on the oral hygiene device 1 indicators 52, or both on an associated mobile device 30 or when accessed on a website hosted or in communication with the server 4.

Figure 4:
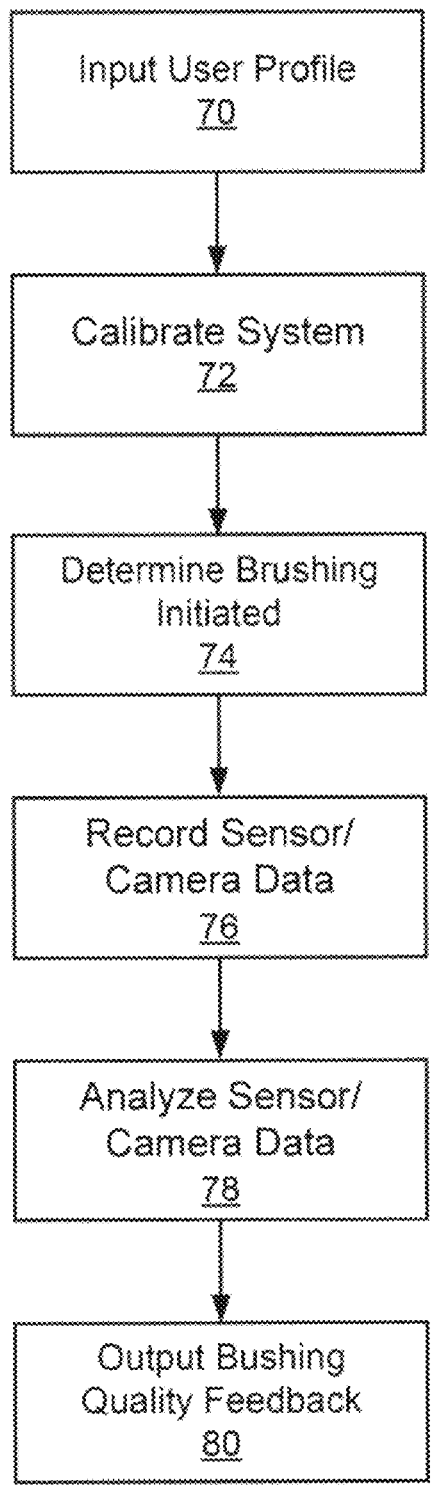
FIG. 4 is a flow chart illustrating an example of a process utilized to record brushing or other hygiene data and provide feedback to the user according to some implementations of the present disclosure.

FIG. 4 illustrates an example of the process by which the oral hygiene device 1 evaluates the brushing quality of a specific user. Each the steps may not be required in a specific embodiment, but various combinations of these steps may be implemented in an oral hygiene device monitoring system 100. First, the user may input a user profile 70 into the oral hygiene device monitoring system 100, to allow the user to calibrate the oral hygiene device 72. In some embodiments, the oral hygiene device 1 may be calibrated at the factory, by the user or both. After calibration, the user may pick up the oral hygiene device 1 and begin brushing her teeth. The oral hygiene device or associated monitoring devices (e.g. camera) would then determine that brushing is initiated 74, and start recording sensor data 76 during brushing. Then the oral hygiene device monitoring system 100 may analyze the sensor data 78 to output brushing quality feedback 80 to the user.

User Profile

Accordingly, a user profile 60 may be entered 70 for each particular user of a certain oral hygiene device 1 or associated with a specific account stored on the server 4, inside the oral hygiene device, base station or other computing devices. Upon initialization for of a new oral hygiene device or new account on the server 4, a user may enter their information that may be utilized to determine optimal brushing times and characteristics. For example, a program 15 may first request a user's name, gender, height, weight, age, and certain questions on their dental history. The user profile 60 may then be associated with certain data recorded during use of the oral hygiene device by the user, including calibration data that is specific to certain oral hygiene devices 1, associated optical sensors 9 or is generic and can be applied to any oral hygiene device 1 or optical sensors 9 connected to the system 100. In some embodiments, a user may upload a picture of themselves, or a program may be initiated that uses the optical sensor(s) 9 to capture a picture of the user from a distance from which a user would typically brush their teeth.

Detecting Usage

A tooth brushing monitoring system 100 may also determine whether usage has taken place and the number of usages per day. In some embodiments, the oral hygiene device 1 and/or optical sensor detection system detects motion data through motion sensors 11 and/or optical sensors 9 and analyzes the data to determine whether usage has occurred, or whether the brush has been moved or usage is feigned.

When motion indicative of usage is detected, the oral hygiene device 1 or optical sensor device 9 may store the positional and motion data in its memory 14 for later analysis. For example, this will prevent the recording of false positives, for example when a user moves the brush in a medicine cabinet, or from children circumventing the system by briefly shaking the toothbrush.

For example, movement indicating usage may be associated with a certain acceleration level and/or frequency that is characteristic of a particular user. In other embodiments, a user may push a button or switch on the oral hygiene device 1, base station 2, or device with an optical sensor/camera 9 to wake up the sensors on the device, which will then begin recording data. Accordingly, the system will determine when brushing is initiated 74. In some embodiments, this will be performed automatically, for example, upon the detection of certain accelerations and frequencies. Accordingly, once the user picks up the toothbrush, the motion sensors 11 may begin recording the data 76 and sending it to any of the various control systems 13 in the system 100 to analyze it 78 for characteristics associated with brushing.

For instance, the oral hygiene device 1 will generally be resting on its base station 2 pointing upwards prior to use, in an orientation that would not be suitable for brushing by a user holding the oral hygiene device 1. Accordingly, once the user picks up the oral hygiene device 1, the oral hygiene device 1 will generally be rotated roughly 45 degrees to be held primarily horizontal during brushing. Accordingly, one threshold criteria for determining that brushing is initiated 74 would be whether the oral hygiene device 1 has been titled within a certain angle range indicating the oral hygiene device 1 is horizontal or near horizontal. This could be an angle range of 20 degrees, 5 degrees, 10 degrees, or other suitable ranges. Additionally, a series of calibration sessions may indicate a suitable range. Of course, this could be detected by optical sensors 9 and/or motion sensors 11.

In some embodiments, the user may turn on the device and the optical sensor/camera 9 (and/or depth sensor) may begin recording. Then the system may look to determine when the pattern 120 is at a certain height indicating it is close to the user's mouth. This may be combined with acceleration information detected by the optical sensor(s) 9 and analyzed as above for the motion sensors 11.

In other embodiments, the determination of whether brushing has initiated 74 and whether or not it has ceased may be performed by the system 100 using a statistical analysis of the motion data from motion sensors 11 and/or optical sensors 9. This statistical analysis may be performed by correlating data from the motion sensors 11 and/or optical sensors 9 to previous tooth brushing or calibration data, or data stored from other users. For example, after performing the analysis, a certain threshold of correlation of the motion data with previously recorded calibration data that is associated with usage may be determined that indicates brushing has initiated 74 or is in progress. Accordingly, once the user begins brushing, the system 100 may record that usage has been initiated 74 and record the data 76 in memory 14 until usage stops as brushing data, for instance after the correlation falls below a certain threshold.

For instance, utilizing an optical sensor/camera 9 system setup, the optical sensor/camera 9 may output data that includes images of the oral hygiene device (e.g. toothbrush or water flosser) and the user. The data may be sent to various control systems to be processed and analyzed for motion. For instance, the image processing algorithms may first determine a boundary condition to identify the boundaries of the lips/mouth of the user, the teeth, the head, the oral hygiene device, the handle, head, bristles, water flosser, etc.

Identifying the boundaries of the human characteristics could be utilized using standard boundary identifying algorithms that generally may utilize threshold changes in certain colors (light frequencies). Once the boundaries of the oral hygiene device 1 are identified, a longitudinal axis could be identified, and potentially an orientation of the bristles (if it is a toothbrush) to determine an angular orientation about the longitudinal axis. This will allow the system to determine the general orientation and motion of the toothbrush, with time stamped frames from the imaging device.

Then, the toothbrush can be identified as on a certain side of the mouth by analysis of the relative positions of the toothbrush and features of the mouth. Furthermore, the orientation of the toothbrush with respect to the side of the mouth it is on can be utilized to determine which section or portion of a user's teeth are being brushed or water flossed. For instance, of the bottom of the upper molars are being brushed on the right side, then the visual system would determine the toothbrush is on the right side of the mouth with the bristles facing up.

Furthermore, once the outline and orientation of the oral hygiene device 1 is determined in each frame, the time stamps of each frame can be utilized to determine the motion of the toothbrush. For instance, the change in positions, (time and distance) can calculate speed and acceleration of changes. Accordingly, as with motion sensors 11, the image data can be utilized determine the motion of the oral hygiene device. Accordingly, that motion may be utilized to determine compliance with brushing or other oral hygiene standards as disclosed further herein.

The analysis of motion data (processed from motion sensors 11 or image data from optical sensors 9) may utilize a fingerprint or signature type analysis that only compares relative movements. The signature may be determined based on the acceleration in certain axes (as detected by motion sensors 11, time stamp image data, or other methods), as the motion of brushing teeth is generally performed in a relatively rapid motion that is uncharacteristic of any other incidental movement of the oral hygiene device 1, for example, to put it back in the cabinet. Additionally, the frequency of the brushing may be monitored, as brushing is generally a rapid periodic motion, and therefore various bandpass frequency, low-pass, and Kalman filters may be used or other techniques to identify certain frequencies of interest and amplitudes in those frequencies that indicate brushing.

These amplitudes in frequencies may be certain frequencies that reach a threshold amplitude, that are associated or determined to indicate a user is brushing. For example, certain frequencies in horizontal or vertical axes may be required for the system 100 to determine brushing is initiated 74, or certain periodic accelerations that reach certain thresholds may be required for the system to determine brushing has initiated 74. In some embodiments, this may a frequency of 1-5 Hz. Once the data analyzed by the controller 13 falls below a certain threshold that indicates use, the system 100 may stop recording data or determine that brushing has stopped.

In addition to statistical analysis, the system may detect movement indicating usage or actual brushing by using filtering and threshold analysis. For example, the system 100 may first filter the data from the motion sensors 11 to pass frequencies only in a certain band (as brushing is periodic) and monitor those frequencies to detect when the for one the signal in that reach a threshold for at least a certain number of cycles or duration to determine the user is brushing. For example, if a user brushes their teeth at an average of 1-5 Hz (or potentially less in the case of a motorized toothbrush), a band pass filter of 1-5 Hz may be implemented.

Thus when the system 100 detects that amplitude of the frequency band in the 1-5 Hz range reaches a threshold indicating use, the controller 13 may begin to record data from the sensors in the memory 14 for the duration of time the motion data indicates the oral hygiene device 1 is being used. Additionally, periodic accelerations in certain axes or angular acceleration (for circular brushing) that reaches certain threshold amplitudes may also be used to indicate brushing has initiated. The analysis of the data may also be affected by whether the oral hygiene device 1 includes an electronic motor to vibrate the head to assist in brushing. In those embodiments, the data may be filtered to eliminate the high frequency acceleration and other noise created by the electronic motor.

Quality of Brushing—Movement Types

In some embodiments, the quality of brushing based of the type of movements the user performs using the oral hygiene device 1 may be determined. Dentists have indicated that certain movements are more or less beneficial for brushing. Different types of movements include circular movements, in both clockwise and counterclockwise motions, tip to root motions, and left to right motions.

In some examples, the system 100 may determine whether the length of the brushing stroke. This could be by any combination of the methods disclosed, including by determining a magnitude of acceleration and time of acceleration in each direction for strokes. For instance, strokes may be filtered out by identifying a regular pattern or filtering at certain frequencies and magnitudes. For instance, acceleration at a certain amount in certain directions with respect to the toothbrush will likely indicate brushing strokes.

Most brushing will take place in the plane of the bristles, because the strokes will be optimized for contact with the tips of the bristles with the teeth using brushing motion. Accordingly, the system may filter out acceleration in the plane of the bristles, or within a suitable tolerance, to further identify acceleration or movement that relates to brushing strokes.

The system 100 may determine if these motions are being performed the relative amount of these motions by filtering the data from motion sensors 11 or optical sensors 9 in certain axes that is indicative of each motion. For example, the data from motions sensors 11 or optical sensors 9 may be filtered in an axis horizontal to gravity, and the control system 13 or other system 100 processors may process the data to determine whether the acceleration, frequency, or other motion data reached a significant enough amplitude in a certain direction to indicate that particular motion is performed.

In the case of image data, in addition to detecting thresholds of acceleration or velocity that indicate brushing, the optical system may detect when the oral hygiene device 1 is within a certain proximity to the user's mouth, or inside the user's mouth to determine brushing is initiated. For instance, if the head can be identified, whenever the head is inside a region defined as being inside the user's mouth the system can determine that the user is brushing his or her teeth quite reliably.

In other examples, acceleration alone may be utilized to determine whether back and forth motions are being used, or circular motions. In other embodiments, the acceleration data from motion sensors 11 may be integrated to determine the actual movement of the oral hygiene device 1 to evaluate the type of brush strokes utilized. The analysis of the data may also be affected by whether the oral hygiene device 1 includes an electronic motor to vibrate the head to assist in brushing. In those embodiments, the data may be filtered to eliminate the high frequency acceleration and other noise created by the electronic motor.

In some embodiments, an electronic motor to vibrate the head 42 may be included in the oral hygiene device 1. In those embodiments, the motion data recorded by the sensors relating to brushing movements would have a smaller amplitude than for a manual brush. This is because users of manual toothbrushes, without the assistance from the electronic motor and moving head 42, will brush their teeth with more vigorous motions. Accordingly, the algorithms utilized to analyze the motion data to detect, use, motion, and location of oral hygiene device will be modified to account for the lower amplitudes and/or different motions, and include filtering of the high frequency noise from the motor. Accordingly, in some embodiments, the thresholds set for the amplitude required to detect or indicate a brush stroke would be less, as a user using an electronic oral hygiene device generally moves the brush at a slower pace, and makes more straight line movements.

Furthermore, pressure sensor 10 may also be utilized to determine whether brushing is actually being performed, or in combination with the motion data from above. For instance, the user may be moving the oral hygiene device 1 around but not pressing on the teeth. Therefore, accordingly, requiring both motion of a certain frequency, amplitude, or features, and a certain pressure will eliminate many false positives from incidental movement or pressure of the brush that is not happening during brushing. Accordingly, the pressure sensor 10 may output a signal that is analyzed 78 by controller 28 to determine a pressure being applied to the teeth. If the pressure is above a certain threshold, the system 100 may indicate or determine it is likely that a user is brushing. This analysis may be performed by statistical analysis, threshold analysis or other suitable calculation methods for determining a likelihood of brushing based on the amount and/or sustained nature of the pressure recorded by pressure sensor 10.

In some examples, the system 100 and oral hygiene device 1 may develop a library of specific types of brushing strokes or motions, and give the user feedback on the brushing strokes or motion the user implemented for their brushing. For instance, the system may retain a dictionary of motion types for tooth-brushing, and rank the motion types, and the quality of each motion type.

Examples of motion types may be the following:

| Type | Motion | Algorithm Examples | Quality |
| --- | --- | --- | --- |
| Horizontal Scrub | Brush along line of dentition in horizontal strokes. Bristles horizontal. | Acceleration in plane of bristles and in one axis switching positive and negative. Bristle axis facing perpendicular to gravity. Machine learning. | Not good: Causes Cervical Abrasion |
| Sulcular Brushing | Place brush tip at 45 degrees and place tips of bristles in gingival sulcus. Vibrate back and forth with very small strokes. | Bristle axis facing about 45 degrees to gravity. Acceleration in plane of bristles and in one axis switching positive and negative. Very small movements. Machine learning. | Very good: removes plaque below the gingival margin. |
| Circular | Move brush in a circular motion. | Continuously changing acceleration in the plane of the bristles. Machine learning. | Least effective brushing technique. |

Identification of Specific Users

The system 100 may include a stored user profile associated with the user's stored tooth brushing (or other oral hygiene) data and the demographic data of the user that includes the age, size and gender of the user. During or after the step of monitoring oral hygiene (e.g. tooth-brushing) activities, the oral hygiene device 1, mobile device 30, or server may automatically seek to match the user with at least one user profile using at least one predetermined rule or algorithm depending on the user profile and of past data. If the user is not a regular user of the oral hygiene device, said user identifies him/her as a guest on the mobile device.

In a step of user identification, a specific user may be associated with the oral hygiene device and presumed to be the user. If multiple users for a given oral hygiene device are utilized, to associate a user with a brushing activity at least in the oral hygiene device and possibly in the mobile device and/or the server at least for reference purposes for those last two.

In embodiments that utilize a camera, the user profile may have a picture of the user uploaded or associated with the profile. This will allow the visual based recognition system to automatically determine a specific user associated with the profile. In some examples, the system 100 may capture a picture with the camera, and identify the specific user by comparing the picture taken initially with each user that initiates brushing. In some examples, the system may utilize the position of the user on the frame of the camera to determine the user (e.g. by estimating the user's height or relative height). In other examples, the system 100 may utilize machine learning and computer vision principles to match features of the user and determine which saved user (and associated user profile) is currently brushing. For instance, eye color or other facial recognition techniques may be utilized to match users on a reliable basis, especially if each unit only has 2, 3 or 4 users total to distinguish.

In other examples, use data associated with a particular user may be utilized to identify that user. For instance, the usage data for a particular user may be associated with a certain acceleration level and/or frequency that is characteristic of that user. For instance, a particular user may have a certain frequency range of tooth-brushing, or may begin on a particular side of the mouth. In some examples, combinations of physical features, motion data, or other indicators may be utilized to identify users and associate the user with their profile data.

Brushing Time and Position

Next, the brushing data recorded above may be analyzed 78 to provide feedback on the positional and time quality of brushing 80. This may be presented after brushing has completed or in real time to provide instantaneous feedback to the user. For example, the motion sensors 11 and/or optical sensors 9 may detect positional information of the oral hygiene device 1. Using the accelerometer and gyrometer data, visually detected data from the optical sensors 9 and patterns 120 or other motion sensors 11, the position, orientation, and movement of the oral hygiene device 1 may be determined and extrapolated to calculate the relative positional movement of the head 42. For instance, if the distance, orientation, and direction of the motion sensors 11 to the bristle portion of the head 42 are known, the system 11 will be able to determine the position of the head 42, and its relative motion, orientation, and coverage area based on the relative motion of the motion sensors 11.

This may be calculated by initially calculating a reference coordinate one the oral hygiene device 1 detects motion, and recording the relative movement with respect to the initial coordinate(s) to determine a signature of the brushing. This may be performed by calculating the movement of the head 42 by calculating the changes in orientation of the brush and the movement due to acceleration recorded by the gyrometer or accelerometer, or visually detected by the optical sensors 9. These calculations may be performed by the control system 13, or other processors that are utilized in the system 100, including a mobile phone processor executing an application on the mobile phone, or a processor(s) on a server running software for analyzing the data.

Brushing Time and Position—Magnetometer

In some embodiments, a magnetometer sensor 11 may provide additional positional information by detecting the polarity, a directional vector and strength of the earth's magnetic field and/or the magnetic field generated by a magnetic field transmitter 110. In some embodiments, this may be a magnetic field transmitter 110 located in the base station 2, as the base station 2 is stationary, and the magnetic field transmitter 110 would have a known polarity and direction (e.g., horizontal or vertical and in a certain direction). This may be detected by a magnetometer 11 located in an oral hygiene device 1. Accordingly, the strength of the magnetic field detected by the magnetometer sensor 11 will give an estimate of the distance the oral hygiene device 1 is from the base station 2 along a sphere or oval curve or egg shaped curve representing the magnetic field lines surrounding the base station 2 or other associated device.

Additionally, the magnetometer will be able to sense the vector direction of the magnetic field along the magnetic field lines. In other embodiments, the distance of the oral hygiene device 1 from the base station 2 may be calculated using: the magnetic field orientation detected by the magnetometer sensor 11 emitted from the magnetic field transmitter 110 together with the attitude information of the accelerometer and gyrometer. This is possible utilizing the knowledge of the shape of the magnetic field and its vectors at particular distances from the transmitter and its polarity. For example, the inclination of the magnetic field with respect to gravity will change predictably at various distances from the magnetic field transmitter for example. Additionally, by comparing the gravity vector with the vector of the magnetic field, the angle may be utilized to calculate the height along the shell or magnetic field lines. This is because the angle of the field with respect to gravity will be different at each height because the egg shell will be directed at a different angle with respect to gravity at each height. This will be especially true when the north and south poles are oriented in a vertical direction, so that the magnetic field lines have components that change from horizontal near the bottom and top of the egg shells to vertical at about the height of the transmitter.

Figure 5:
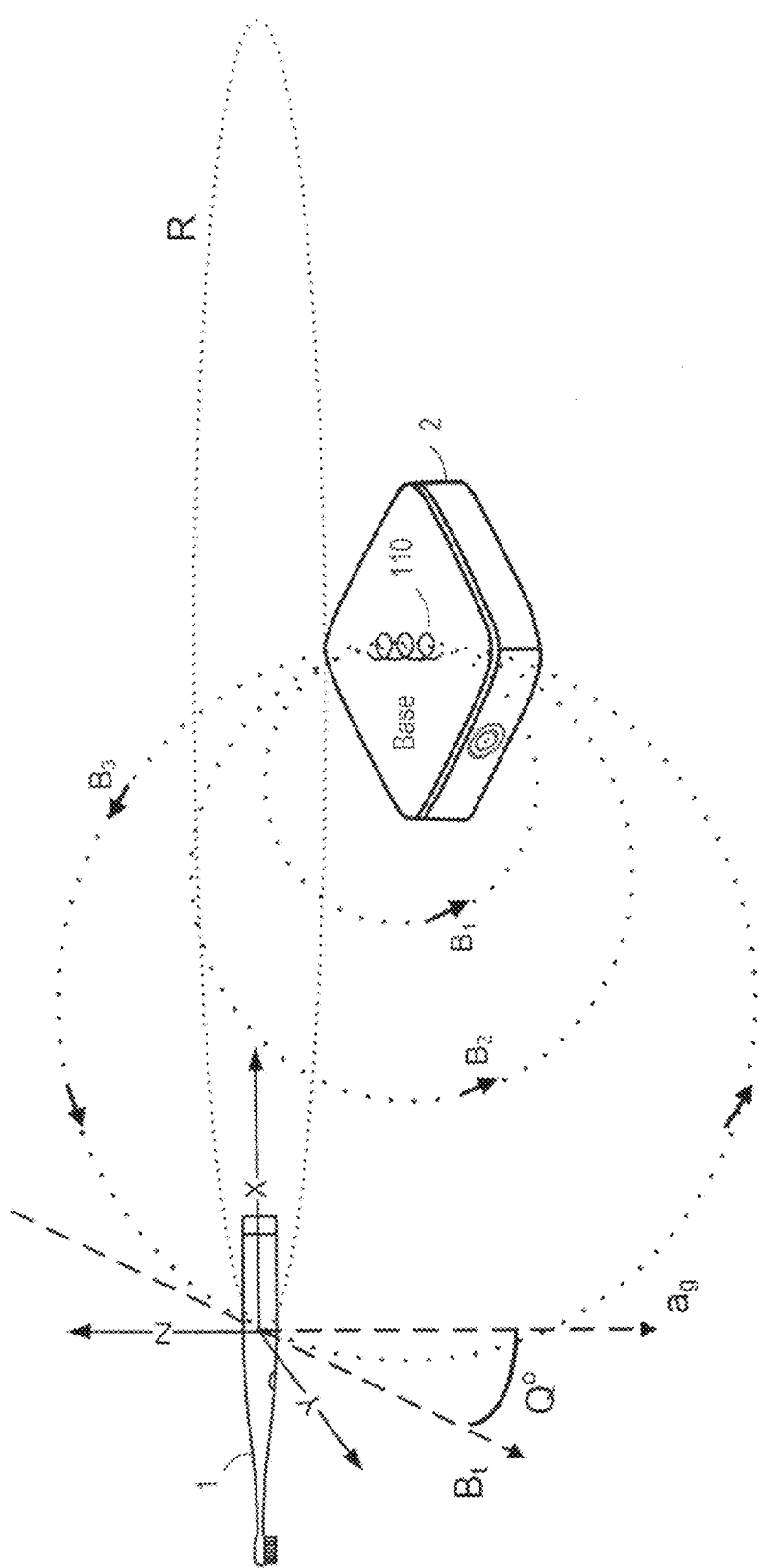
FIG. 5 is diagram illustrating an example of an oral hygiene device and base station, with a magnetic field generator in the base station or other associated device.

Accordingly, the magnetometer data combined with the accelerometer data and/or optical data may be utilized to determine position of an oral hygiene device 1 within a ring that is situated in a horizontal plane that is of equal magnetic field strength around the transmitter 110. For example, FIG. 5 illustrates an embodiment of a base station 2, with a single coil magnetic field transmitter 110 that generates shells that have slices with B (magnetic) field vectors that change direction in a vertical plane. Sensors 11 on the oral hygiene device 1 may include a magnetic field sensor 11 to detect the magnetic field generated by the magnetic field transmitters 110 and an accelerometer 11 to detect, among other accelerations, the acceleration of gravity $a_g$. Accordingly, the magnetometer 11 on the oral hygiene device 1 may be positioned with the B field generated by the transmitter 110. Accordingly, a magnetic field strength and direction ($B_t$) may be determined by the magnetometer 11. Simultaneously, an accelerometer 11 may detect the acceleration from gravity as vector $a_g$. The system 100 may the analyze that data, and determine an Q° between the gravity vector $a_g$ and magnetic field vector $B_t$.

The angle Q° may then be able to be used to determine a ring R wherein the oral hygiene device 1 position is known to be at some point along ring R. For instance, first, the strength of the magnetic field B detected by the magnetometer 11 can be utilized to determine which magnetic field egg or donut shaped shell the oral hygiene device is on (e.g., $B_1$, $B_2$, or $B_3$). This would narrow the position of the oral hygiene device 1 down to a hollow shell or donut surround the transmitter 110. Next, Q° can be unitized to calculate a vertical position on the shell or donut and therefore narrow the position down a ring R surrounding the transmitter 110. Accordingly, if the system 100 detects movement to a new ring R, the system will have information about the possible direction and distances travelled. This information will be enhanced by the accelerometer data, which will provide further information about the direction travelled. This, for example, may provide certain upper or lower bounds of direction and/or distance travelled by the oral hygiene device 1. Thus, this system 100 and data processing technique may be utilized to provide relative position and movement information of the oral hygiene device 1 and applied to determine tooth brushing position in the mouth as described herein.

In some embodiments, a magnetometer sensor 11 may sense a magnetic field transmitted by a magnetic field transmitter 110. In order to do this, this magnetic field data must be filtered out from extraneous noise and especially from the earth's magnetic field. The earth's magnetic field will be of relatively constant strength and direction at a given location on the scale of movement of a toothbrush. Additionally, the earth's magnetic field is quite large and most magnetometers are calibrated to the scale of the earth's magnetic field. Accordingly, to use a magnetometer calibrated for the earth's magnetic field, for instance, in embodiments that detect both the magnetic field of the earth and of the transmitters 110 to calculate orientation and position changes, certain filtering algorithms must be used to distinguish the two. In some embodiments, the critical data that may be utilized to filter the two is that the strength of the earth's magnetic field remains relatively constant on the scale of oral hygiene device movement, compared to the change in magnetic field detected that is transmitted by the magnetic field transmitter 110. Therefore, temporal filters may be applied to distinguish the two magnetic fields. In some embodiments, the magnetic field transmitted by transmitter 110 may be pulsed at a certain frequency or amplitude in order to be easily filtered out using signal processing and data analysis.

In some embodiments, the magnetic field directional component of the vector data output from the magnetometer 11 may also be utilized to calculate a relative position change and/or orientation. For example, in some embodiments, the transmitter 110 may transmit a magnetic field with a vector orientation illustrated in FIG. 5. Directional or vector information detected by a magnetometer from a magnetic field B created by transmitter 110 may be useful to provide orientation and or relative positional information. This data may then be combined with data from the directional vector information detected from the earth's magnetic field which would likely have an orientation that differs from the orientation of the earth's magnetic field. Accordingly, the magnetometer 11 may detect vectors indicating the direction of the earth's magnetic field and the vectors of the magnetic field of the transmitter 110 to provide a reference for orientation in space and for changes in position.

In one example, the magnetometer sensing the earth's magnetic field could sense an orientation of the oral hygiene device 1 in a horizontal plane as would a compass or about the Z axis illustrated in FIG. 5. In some embodiments, this may include a vector not only in the horizontal direction but in the vertical direction that will be constant and based on the inclination of the earth's magnetic field at a particular geographic location. In other embodiments the transmitter 110 may be placed in a diagonal, horizontal, vertical or other known orientation which is used as a reference point to calculate orientation of the magnetometer 11 and positional changes of the magnetometer 11 and oral hygiene device 1.

Furthermore, calibration may be necessary based on the relative orientation of the oral hygiene device 1 when being used by a user and the base station's magnetic field transmitter 110. As the shape and orientation of magnetic field lines change based on the position with respect to the magnetic field generator, different formulas, calibrations, or adjustments may need to be performed. For example, near the side of a magnetic field generator, the flux lines may be oriented in a first direction; however, near either polar end of the transmitter 110 (e.g., above or below, or the right or left side) the flux lines may be oriented perpendicular to the first direction near the side or middle of the transmitter 110. Additionally, the user may be required to brush her teeth a certain distance from the transmitter 110 to ensure a proper magnetic field for measuring is generated in that position. The beneficial aspect of the coils being physically oriented in the vertical direction is that the magnetic field generated is relatively the same on all sides of the transmitter 110 (and by proxy, the base station 2) assuming relatively the same height, and therefore calibration may require simpler algorithms and/or processes. However, if the coils lie in a horizontal plane, depending on the orientation of the base station 2, the magnetic flux lines may be traveling in different directions. In that embodiment, the user may be instructed to swivel the base station 2 to point it in a certain direction with respect to the user where the user typically brushes their teeth. In other embodiments, the calibration may be able to utilize or accommodate for changes in the vector direction of the magnetic field transmitted by the transmitter 110.

The data from a magnetometer 11 may be combined with the data output from an accelerometer 11 or data from the gyrometer 11 and accelerometer 11 or optical sensor/camera 9 to determine orientation and/or position. For example, the accelerometer 11 and/or optical sensor/camera 9 data may first be utilized to determine the orientation of the oral hygiene device 1 with respect to gravity during periods of relatively little acceleration, so the acceleration of gravity would be detected by a three axis accelerometer or image analysis so it could be determined whether the oral hygiene device 1 is tilted about a lateral axis that is in a horizontal plane, or how it is rotated about a its longitudinal axis (a longitudinal axis running lengthwise through the toothbrush) with respect to a gravity pointing down towards the earth.

If the accelerometer data indicates the oral hygiene device 1 is experiencing relatively small amounts of acceleration relative to normal tooth brushing movements, the control system may determine that the oral hygiene device 1 is relatively still and the accelerometer data can be utilized to determine a vector oriented in the direction of gravity.

If the accelerometer data is combined with the gyrometer data, deviations of the attitude of the tooth brush with respect to gravity can be determined to calculate the attitude of the toothbrush. For example, the initial recording of the gravity vector may then be used as a reference vector to determine attitude. Then deviations from this initial position or attitude determined by the accelerometer and gyrometer may be determined by calculating orientation changes from the initial reference vector based on gyrometer data. Accordingly, the accelerometer or accelerometer and gyrometer data may be utilized to determine which way the bristles are facing. For example, in some embodiments, the accelerometer and gyrometer data may be analyzed to determine whether the bristles are facing upward forwards or downwards, front, left and right side, potentially narrowing down to a specific quadrant or other division of the mouth. For example, when the oral hygiene device 1 bristles are facing down they could only be brushing the tops of the bottom teeth. If the oral hygiene device 1 bristles are facing up, it could only be brushing the crowns or tips of the upper teeth. As a further example, when the oral hygiene device 1 is facing right, it could only be brushing the left sides of the molars, etc. Additionally, in some embodiments, the orientations with respect to gravity will be deterministic as a vector representing gravity always points in the direction towards the floor or earth, and brushing will very likely take place standing up straight.

Therefore, it is possible to determine the orientation of the bristles with respect to the teeth in some aspects or planes of orientation. In certain embodiments, these calculations may be made deterministically, or estimated using statistics and/or a retrofitted model of the mouth. For example, if the accelerometer senses the toothbrush's bristles are facing down within a certain margin of error or within a statistically significant margin, then the system can determine that the surfaces being brushed are likely the tops of the lower teeth (or the tongue for example). In other embodiments, as disclosed herein, the brushing orientations may be calculated relative to each other, so a model of the mouth may be fit each time the user brushes their teeth.

To determine the orientation in a horizontal plane perpendicular to gravity, the earth's magnetic field or the magnetic field generated by the base station 2 transmitter 110 for example, may be utilized. In some embodiments, the magnetic field transmitter 110 will generate a magnetic field with directional vectors that change direction in a horizontal plane that is perpendicular to gravity. Accordingly, even if the absolute direction is not known, a relative orientation of the oral hygiene device 1 with respect to the magnetic field detected by the magnetometer 11 and emitted by the transmitter 110 may be determined in a horizontal plane. Accordingly, relative changes of this orientation in a horizontal plane could be determined and a path of movement along a reference coordinate system may be determined. In some embodiments, the reference coordinate system may be based on one of the initial or any other data points recorded during a tooth brushing session. As disclosed herein, these relative changes may be utilized to calculate the positions or reconstruct the shape by using relative positions after a user is finished brushing.

In some embodiments, data from the gyrometer, magnetometer, optical sensor and accelerometer may be utilized to determine an orientation with respect to gravity and either or both magnetic field of the earth and of the transmitters 110. In some embodiments, orientation may be determined and confirmed or validated by the different sensors 11 or optical sensors 9. For example, the angular velocity from a gyrometer may be integrated to determine orientation changes in certain directions, but errors from integration may be corrected using the magnetometer readings and/or optical sensor/camera 9 data. In other embodiments, either or both the magnetometer, gyrometer and magnetometers may be utilized in various combinations to determine orientations.

In some embodiments, orientation alone may be utilized to determine the position of the oral hygiene device 1 using statistical analysis as disclosed herein. In other embodiments, the gyrometer and/or accelerometer detected inertial changes may be used in conjunction with or separate from magnetometer 11 readings to be provide further indications of movement or distance to calculate an estimated position of the oral hygiene device 1 bristles. In some embodiments, the orientation information may be combined with data output from sensors 11 or optical sensors 9 that indicate translational inertia, or positional changes. Depending on the location of the inertial sensor, the orientation information may be combined with the inertial movement data to indicate the position of the bristles. For instance, if a motion sensor 11 is located inside the oral hygiene device 1, but in the middle of the toothbrush's longitudinal axis where the user would hold the oral hygiene device 1, changes in orientation would move the head without moving the position (although it may rotate in place) of the motion sensor 11. Accordingly, the orientation information can also be used to calculate a position in space of the bristles relative to the position of sensor 11.

Movement or positional changes may also be calculated from data output by the magnetometer 11. In some embodiments, the magnetometer 11 may detect a magnetic field generated by a magnetic field transmitter 110 in the base station 2 or another stationary component that is separate from the oral hygiene device 1. In this embodiment, the strength and orientation of the magnetic field sensed by a single-, two-, or three-axis magnetometer 11 can provide additional data on the positional movement of the oral hygiene device 1 with respect to the magnetic field transmitter 110 in the base station 2, which is fixed and stationary. Accordingly, the increase or decrease in magnetic field will indicate that the oral hygiene device 1 is moving towards or away from the base station 2. Additionally, changes in the orientation or inclination of the magnetic field and its polarity output by the magnetometer 11 can be utilized to determine translational and position. This information may be utilized to determine, based on calibration or experimental data, how much a per unit change in magnetic field strength is equivalent to in distance based on the direction of movement (as different directions through a magnetic field will have higher or lower rates of change). In other embodiments, the per unit change in inclination or shape of the magnetic field may also be correlated to changes in position. The respective orientation of a horizontal magnetic field may be different each time a oral hygiene device system as disclosed herein is set up, including such a system that incorporates a magnetometer in the base station 2. This is because how each user stands as they are brushing their teeth, and/or how the base station 2 is oriented on the top of the counter may change for each user and even change somewhat each time and after cleaning the countertop, etc. Accordingly, adaptive statistical analysis may be utilized to determine relative positions of the bristles of the oral hygiene device 1.

Positional data calculated from magnetic field data output from a magnetometer 11 may be combined with inertial data to calculate positional changes in the oral hygiene device 1. In some embodiments, the inertial data may be utilized to calculate distance traveled and the magnetometer data may also be utilized to eliminate errors, and/or provide bounds to the calculations for positional changes based on the inertia data. For example, the changes in magnetic field strength may have a certain minimum lower bound limit assuming travel directly perpendicular to the magnetic field lines where they are most compressed. Given a certain change in magnetic field strength, it could be determined that the magnetometer had at least travelled a certain Euclidean distance in space (or changed a certain angular orientation). These changes in inclination and field strength may be utilized to determine distance changes within certain margins of error that may be supplemented or fine-tuned according to accelerometer or gyrometer data. This data could be combined with orientation and inertial data to determine a more precise distance travelled and relative directional travel of the oral hygiene device 1.

Brushing Time and Position—Visual Pattern Recognition

An optical sensor/camera 9 and pattern 120 recognition system may be utilized, in some embodiments, to track the movement of the oral hygiene device 1. For instance, as described above, the oral hygiene device 1 may contain patterns 120 on the handle 40 or head 42 that can be recognized by a visual tracking system. The visual tracking system may be able to recognize the orientation, distance and position of a pattern 120 that is on the oral hygiene device 1. For example, in some embodiments, the pattern 120 may be both on the head 42 and a separate pattern 120 may be on the handle 40 to allow the system to determine the position of both the handle 40 and the head 42 of the oral hygiene device 1 to assist in determining the orientation and movement. Visual pattern recognitions have been utilized to detect the movement and orientation of markers, such as for example the system described in "Towards Positioning through Visual Markers," by Bernhard L. Ecklbauer, the disclosure of which is incorporated by reference in its entirety. For instance, image processing software may identify the boundaries of the oral hygiene device by standard boundary image identifiers, identify objects the appropriate dimensions and size for a toothbrush, and then attempt to determine an orientation of the oral hygiene device (or determine an orientation of the pattern 120 and the oral hygiene device respectively).

In some embodiments, the visual pattern recognition system may also be utilized to determine the position and orientation of the human face. This will be useful to compare the relative position and orientation of the face and/or mouth and the oral hygiene device 1 in order to determine the position of the oral hygiene device with respect to the mouth. In some embodiments, the system may first acquire an image with the oral hygiene device 1 at the same distance from an optical sensor/camera 9 as a human face. Additionally, an initial calibration using the orientation and size of the face may be utilized to calibrate the distance from the camera 9 to the oral hygiene device 1, so size and movement can be estimated. In some embodiments, since the size of the oral hygiene device 1 is known, the relative size of the face using the oral hygiene device 1 could be determined, to calibrate or estimate the jaw shape and size and modify the algorithms utilized to determine which zone is being brushed.

For instance, the system could determine whether the oral hygiene device 1 is in or near the mouth if the system can be utilized to determine the position and orientation of the face. This will help the system validate and confirm when usage starts and stops, as the oral hygiene device 1 would only be near the mouth of the user is actually using it. Rarely would a user hold the brush near the mouth when they are not actually brushing their teeth. Rather, a user generally immediately washes it off/puts down the oral hygiene device after they finish brushing.

Accordingly, the data detected by the camera can be evaluated to determine the position, movement and orientation of an oral hygiene device 1. For example, an oral hygiene device 1 may have a code "AB" with a circle and line as illustrated in FIG. 6 either on the back of the head 42, or on the handle 40, or both. In some embodiments, the pattern 120 could be any other pattern 120 that has a distinct orientation as described herein. The camera 9 may detect the pattern and the data may be retrieved for processing and analysis. For example, the visual data detected by the camera may be output and a processor may evaluate the data to determine the orientation and size of the pattern 120 and the relative sizes of certain parts of the pattern 120.

For instance, if the pattern is AB and it is oriented as pictured on the back of the head 42 of the oral hygiene device 1 and the data analysis determines that the AB is oriented upright, then it is likely that the user is not brushing their teeth. This is because this will mean the oral hygiene device 1 itself is upright (as pictured in FIG. 6) which would be a highly unlikely position for a user to hold an oral hygiene device 1 to brush their teeth. Rather, the longitudinal axis of an oral hygiene device 1 will generally be held in a horizontal plane during tooth brushing. However, if the camera 9 detects data that indicates the AB on the head of the oral hygiene device 1 is sideways, it likely means two things: (1) the oral hygiene device 1 is positioned that the back of the head 42 of the oral hygiene device 1 is facing the user because the AB is actually visible to the camera 9 and (2) the oral hygiene device 1 is horizontal because the AB is oriented on its side. This, for instance, would provide a high likelihood that the oral hygiene device 1 was brushing the front incisors. This is because the camera 9 is generally positioned so that the user is facing the camera 9 as they brush their teeth. Accordingly, if the AB is visible to the camera 9 and lying on its side, then the oral hygiene device 1 must be oriented with the bristles facing the mouth (to brush the front surfaces) and brushing the front teeth (rather than the sides) because the AB is still visible to the front facing camera 9.

In many oral hygiene device 1 positions, however, the head 42 of the oral hygiene device 1 and any associated pattern 120 may not be visible to the camera 9. For instance, when brushing the molars, tongue, top or bottom surfaces of the teeth, a pattern 120 on the back of the head 42 would not be visible. Accordingly, in some embodiments, an additional pattern(s) 120 could be included on an attachment 130 on the end of the oral hygiene device 1. This would allow the camera 9 to detect the orientation of the pattern 120 on the attachment 130 and/or handle 40 while the oral hygiene device 1 is in inserted inside the user's mouth. For instance, in some embodiments, the attachment 130 may be a spherical shaped bulb on the bottom of the handle 40 of the oral hygiene device 1, and would include several different patterns in different positions around the sphere.

This would allow the camera to detect the position and orientation of several different patterns. Upon visually detecting a pattern, the system could determine (1) which pattern 120 is being detected, (2) the size of the pattern 120, (3) the orientation of the pattern 120, (4) the relative size of different components of the pattern 120, (5) other characteristics of the pattern 120. This information could be downloaded and compared to existing data regarding the types and orientation of patterns 120 that are placed on the attachment 130 (and/or handle 40 or head 42 of the oral hygiene device 1). For example, the system may include a database that stores each of the different patterns 120 and different size and orientation information with respect to the pattern 120 in relation to the oral hygiene device 1 and distance from the camera 9. For example, each pattern 120 may include information about if it is found in an upright orientation, then the oral hygiene device is on its side, pointed in the mouth, etc. In other embodiments, the size of the pattern 120 detected may be equated to the distance of the oral hygiene device 1 from the camera 9, assuming a set distance. In some embodiments, calibration information may be further added to enhance the systems analysis of brushing data for a particular individual and/or a particular bathroom. Therefore, each pattern 120 may have a pixel number associated with each component (e.g., height/width of certain features) that may be associated with a certain distance from the camera 9. This may be an approximate or average, or use statistics to find the distance/orientation of the highest probability.

Then, once this pattern information is determined, it could be compared to calibration information or other data representing the patterns 120 and respective orientations that are included on the attachment 130 for example. If for example, an AB pattern 120 is included on the attachment 130 as illustrated in FIG. 6, with an upright orientation and facing forward in the same direction as the bristles, the if this pattern is detected upright, it is unlikely the user is brushing their teeth. However, again, if this pattern 120 is detected with a sideways orientation, it is likely the user is brushing their front molars. In another example, if another pattern, BC is placed on the bottom of the toothbrush, when the system detects that pattern it is likely that the oral hygiene device is being used to clean the molars. Accordingly, the orientation of the BC could then be used to determine whether it is likely the user is cleaning the tops, bottoms, or sides of the molars. In some embodiments, this could be combined with accelerometer and gyrometer data to determine which side of the mouth is being brushed.

In still another embodiment, the system may be able to determine the position of the oral hygiene device (without a pattern) with respect to the face, including the vector direction of its longitudinal axis. Accordingly, the system could then determine whether the oral hygiene device is likely on the left or right side of the mouth. This could be done using the visual recognition system as disclosed herein. In other embodiments, the system could determine the position and orientation of the mouth and oral hygiene device with respect to each other. For instance, a mouth recognition algorithm could be used to approximate the position of each of the corners or sides of the mouth. Additionally, there could be visual markers on the neck of the oral hygiene device 1 to help the system determine which side of the mouth is being brushed when the user has the oral hygiene device inside the mouth.

No Pattern on Toothbrush

Figure 7:
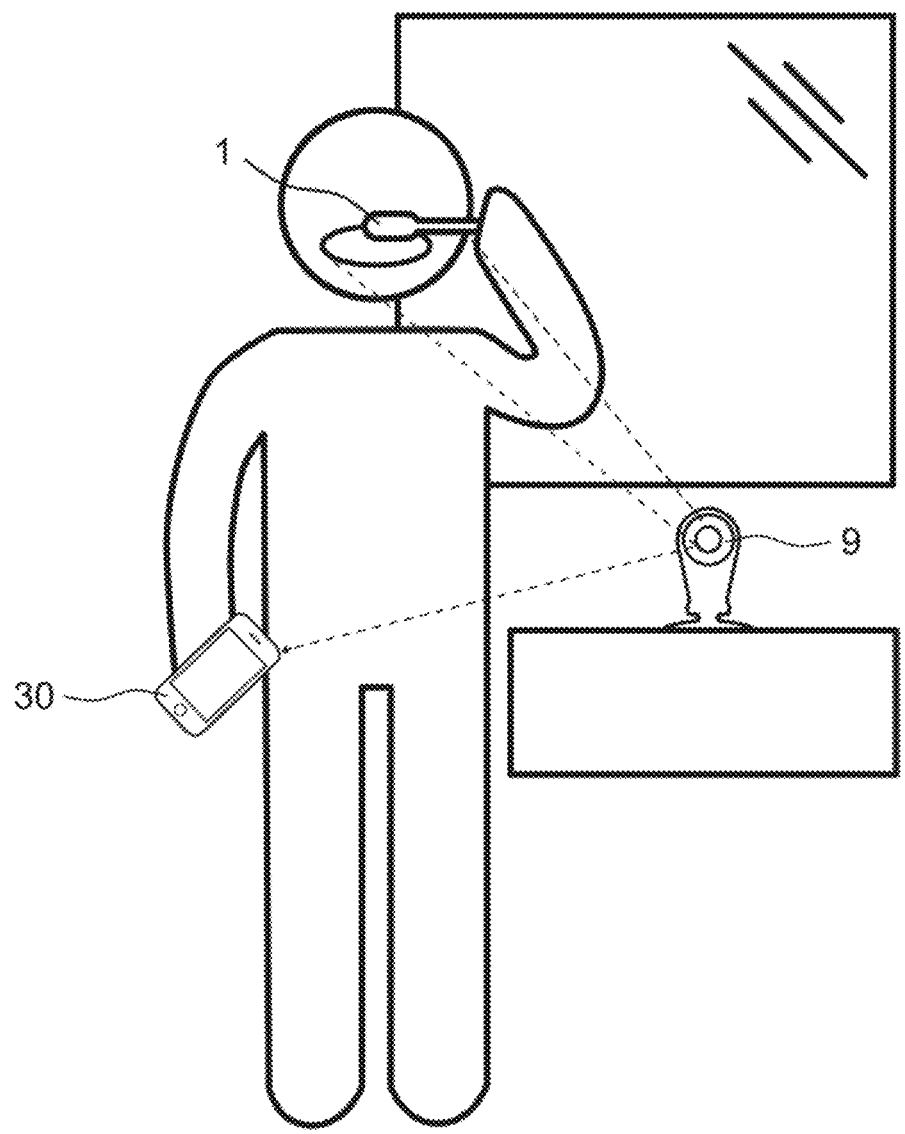
FIG. 7 is a perspective view illustrating an example of a system that identifies the position of the oral hygiene device visually without a pattern.

As illustrate in FIG. 7 and in some embodiments, the system may only detect the outline of the oral hygiene device 1 handle to determine an orientation of the longitudinal axis with respect to gravity with without utilizing a pattern 120, or markings. In other embodiments, the system may have additional image processing software to identify specific features of the oral hygiene device including the head (bristles, etc.) by utilizing classification algorithms to classify certain portions of the image. In some embodiments, the image processing software identifies the longitudinal axis, the head, the base and potentially the bristles. From this information, the orientation and position of the oral hygiene device may be determined. In some embodiments, the user and the mouth of the user may be identified utilizing similar boundary detection/shape classification software. Accordingly, the relative position of the oral hygiene device with respect to the mouth may be determined, as explained further herein.

The inventors may utilize this system so that a customized oral hygiene device is not necessary, and only a chip would need to be provided inside the oral hygiene device that includes motion sensors 11. Accordingly, the device could be manufactured utilizing an existing oral hygiene device designs and only implementing a chip or controller 13 system that includes a motion sensor 11, antenna 5 or other wireless connectivity, and a memory. Then the device could send all of the data to a connected smartphone or other connected device 30 (e.g. smart mirror, etc.)

Combining Visual and Motion Data for Position Determination

The visual data may also be used to determine acceleration and the vector or direction of motion of the oral hygiene device 1 as it is brushing the teeth. The visual data may capture the different positions and time stamp the data to determine the amount of time recorded to travel for a first point to a second point and therefore the resultant velocity (direction and speed) and acceleration. As described herein the positional data may be utilized to calculate brushing positions. This combined with the orientation data will be able to provide enough positional and orientation data to determine the position in a user's mouth and the section of the mouth that is being brushed as described herein.

For instance, in some embodiments, the visual information from pattern recognitions or brush outlines may be utilized to recalibrate or the position output from the accelerometer/magnetometer/gyrometer position determination. In these embodiments, the visual data may be utilized to recalibrate the drift experienced by the position sensors to bring them back to a reference coordinate system. In other embodiments, the visual data may be utilized to recalibrate the entire statistical model used to determine position.

In some embodiments, position may be independently determined from motion/acceleration/position sensors, and independently determined from visual recognition data. These two determinations may then be utilized to determine a final position with respect to the mouth. In other embodiments, just the visual recognition data alone may be utilized to calculate position with respect to the mouth.

For instance, a first example would a setup with no visual pattern 120 added to the oral hygiene device 1. Using data output from the motion sensor(s) 11 only, it may be challenging to distinguish, in some situations, which side of the mouth the oral hygiene device 1 is on when the oral hygiene device is oriented in the same direction but could be brushing different sections of teeth. For instance, its orientation about an axis is identical or near identical, but its position on one side of the face, is on the left or the right side of the mouth.

For example, an ambiguous determination could be: is the user brushing the outer face of the teeth on the left side of the mouth, or is the user brushing the inner face of the teeth on the right side of the mouth? Even with no additional visual pattern 120, with visual information of the oral hygiene device and the user's face alone the system can make a distinction between left and right. So, the combination of algorithms in this case is beneficial in that inertial data is known to be insufficient to establish a relative spatial position on a coordinate system surrounding the head. Thus, the visual information can be utilized to make a secondary determination of which side of the head the brush is on, and therefore, the visual information and the orientation information (about an axis or point or with respect to gravity) can be combined to determine which side of the head the oral hygiene device 1 is on and whether (for example the inner or outer face of the teeth are being brushed).

Another example may include an embodiment with a pattern 120 attached to the oral hygiene device 1. For instance, a pattern 120 could be added to the bottom of the oral hygiene device 1 and to the back of the oral hygiene device 1 head. With a pattern 120 however, there may be positions of the oral hygiene device 1 in which visual information alone would not be enough to determine the location and orientation of the oral hygiene device 1 with enough accuracy. For example, when the visual tags are partially hidden, or too small in the image resolution to be accurately detected in size and orientation.

For example, if a user is brushing the molars, and the only visible pattern 120 is on the oral hygiene device 1 bottom, and the resolutions is low (e.g., because the user is a bit too far from the camera device, or because the user is using a camera that has insufficient resolution) then the system may not be able to determine with enough accuracy the angle with which the oral hygiene device 1 is on the teeth. Therefore, the system could not determine whether the user is brushing the outside of the molars of the upper jaw or the outside of the molars on the lower jaw.

In this case, the angle difference (e.g. the angle of the longitudinal axis of the oral hygiene device with respect to gravity because you hold the oral hygiene device at a slightly different angle when brushing the top or bottom molars) may be quite subtle between those two brushing positions. However, the motion data (especially acceleration and vertical orientation) may be able to disambiguate the two potential positions narrowed down by the visual data and hence provide the necessary information to if the oral hygiene device 1 is brushing the upper or lower jaw. Accordingly, the visual data alone can be supplemented with the motion data to determine the position or section of teeth that are brushed.

Brushing Time and Position—Analysis of Motion Data

In order to utilize the data from the sensors to estimate the amount of time spent in each section, quadrant or other logical division of the mouth, the user may need to calibrate the oral hygiene device 1. In some embodiments, calibration may take place at the factory, by the user or both. Accordingly, calibration could be utilized to calibrate a specifically manufactured unit, and to adapt to a particular user's geography, anatomy (i.e. height) and/or bathroom environment, which for example, may include unique magnetic interferences unique heights and orientations (tabletops may not be level, etc.). For example, in some embodiments, the user may apply a colored gel to their teeth. The user can then turn the oral hygiene device 1 in calibration mode once the oral hygiene device 1 is in position in by the teeth and brush away all of the colored gel, while the motion sensors 11, optical sensor(s) 9 and other sensors are recording data.

At this point, the user may switch off calibration to stop the acquisition of calibration data. In other embodiments, once the user turns on the calibration function, the oral hygiene device 1 would detect the points in time when the user has started and stopped brushing, including any pauses in the brushing. This calibration procedure provides reference positional, orientation, and motion calibration data that can then be compared to subsequent brushes using statistical analysis 78, or other analysis methods to determine whether subsequent brushes have brushed all regions of the mouth for sufficient time.

Once the device is calibrated, or using reference data from previous brushing or and other model users brushing, brushing data from each usage may be compared to reference data to evaluate its quality 78 and determine the position of the oral hygiene device 1 in the newly acquired data. For instance, the calibration data may be utilized to prepare a statistical model of the shape and dimensions of a specific user's mouth and be used to create certain statistical boundaries for determining when the oral hygiene device 1 is brushing any certain section of the user's mouth. Then, once a user initiates brushing a second time, the newly recorded data could then be overlaid or correlated with the calibration brushing data associated with that user profile 60, to determine whether and where there were any deficiencies in the brushing. For instance, the system 100 may determine how much time is spent brushing each quadrant, how many strokes, or perform other evaluations of the brushing. Additionally, the analysis may indicate that a user brushed too much in certain areas or did not use the correct stroke patterns generally or in specific sections of the user's mouth.

The correlation may be performed by statistical analysis, for example, a quantitative comparison of such differences can be made simply by measuring the Euclidean distance in the 3xz space. Such vectors may then be treated by using a statistical analysis, including principal component analysis (PCA), hierarchical cluster analysis (HCA), regression analysis, and linear discriminant analysis. Statistical methods suitable for high dimensionality data may be utilized. As an example, HCA systematically examines the distance between the data that represent each type of motion or positional data. A dendrogram can then be generated that shows the clustering of the data from the Euclidean distances between and among the data vectors, much like an ancestral tree.

Each statistical data cluster may be representative of sensor data for each section, quadrant or other logical division of the user's mouth. For example, the mouth may be divided into, top and bottom, with top and bottom each having a right front and left portion, and each of the right, front and left portions, having an inside, top, and outside face. Accordingly, the mouth may have 36 different sections, 10 sections, 8 sections, 12 sections, or 4 sections (quadrants), top and bottom only, outer and inner only, and other logical divisions. Accordingly, using reference data, the controller 13, or other processors in the system 100 (e.g., processors in the mobile phone or servers), may calculate the confidence interval or other value indicating the likelihood the oral hygiene device is brushing a specific section of the user's mouth, but determine the likelihood the strokes correlate or relate to the calibration data in those sections. In order to acquire a reference position, the user may be instructed to initiate brushing at an identical position of the mouth. That way, the data starts at a known position and can use that as a reference point to relate the rest of the data using statistical analysis. For instance, the angle, orientation, calculated distance and other features from the reference position of the oral hygiene device 1 detected by the motion sensor 11 and/or optical sensor/camera 9 may indicate the likelihood each new position is correlated to a certain position of the mouth based on calibration data.

In other embodiments, the control system 13 or other system processors (e.g. processors in the smartphone, servers, or other components) may process the statistical data and determine that the brush is brushing a certain section of the mouth if the statistical analysis shows with great than 95%, 85%, 80% or other suitable certainty that the brush is within the section of the mouth. In some embodiments, the specificity or sensitivity of the brushing statically analysis may be modified to match a specific user's variance.

This analysis may include an output 80 that allows the control system 13 or other processors to determine which brush strokes were in each section of the mouth or tooth set, and therefore how much time a user spend brushing each quadrant, half or tooth, or other logical division of the mouth and how those times compare to recommended regimes. In other embodiments, the time at the beginning and end of entering a certain area may be recorded, or other suitable methods to determine how much time is spent brushing each section of the mouth.

In some embodiments, rather than detect the position of the toothbrush, the system 100 may direct the user to brush certain sections of the mouth one at a time, and only determine whether or not the user is actually brushing, and count or record brushing time only while motion indicative of brushing is detected. Then, once brushing has been recorded in the directed section for the prescribed time, the system 100 would indicate to the user that it is time to move to the next section of the mouth, and elapse time when the user is actually brushing. This prevents the user from taking breaks and thereby brushing for less than the optimal amount of time in each section. Accordingly, the control system 13 or other processors may analyze the data from the sensors 11 (or pressure sensor 10) to record the amount of time the user was brushing in each section while the system 100 indicated the user should be brushing in that particular section.

In other embodiments, pressure exerted on the head 42 from brushing may also be detected by a pressure sensor 10 incorporated into oral hygiene device 1. For example, the pressure sensor 10 may be incorporated into the head 42, and detect a pressure associated with usage. Additionally, the pressure may be mapped to the various positional data and therefore the controllers 13 or other processors of the system 100 may calculate the amount of pressure utilized for brushing each area of the mouth.

Machine Learning

In some examples, the statistical analysis utilized to implement various features disclosed in the system 100 will be a machine learning or artificial intelligent algorithm. For instance, the system 100 may process the available data sources from the systems 100 sensors included as disclosed herein, and identify a position within the mouth. In other examples, machine learning algorithms may be utilized to: (1) identify cavities or plaque using machine vision or other combinations of data, (2) identify position in the mouth to varying degrees of granularity, (3) identify bush stroke type using the dictionary of strokes disclosed herein, (4) identify users from motion or image data (e.g. machine vision to recognize facial features), or (5) other useful applications to the features described herein.

Machine learning algorithms may take a variety of forms. For instance, the system 100 may utilize more basic machine learning tools including 1) decision trees ("DT"), (2) Bayesian networks ("BN"), (3) artificial neural network ("ANN"), or (4) support vector machines ("SVM"). In other examples, deep learning algorithms or other more sophisticated machine learning algorithms may be used.

DT programs are generally used because of their simplicity and ease of understanding. DT are classification graphs that match input data to questions asked at each consecutive step in a decision tree. The DT program moves down the "branches" of the tree based on the answers to the questions (e.g., First branch: Is the patient male? yes or no. Branch two: Is the patient having trouble urinating? yes or no. etc.).

Bayesian networks ("BN") are based on likelihood something is true based on given independent variables and are modeled based on probabilistic relationships. BN are based purely on probabilistic relationships that determine the likelihood of one one variable based on another or others. For example, BN can model the relationships between symptoms and diseases. Particularly, if a patient's symptoms or biomarkers levels are known, a BN can be used to compute the probability that a patient has a particular disease. Thus, using an efficient BN algorithm, an inference can be made based on the input data. They are commonly used by the medical domain to represent reasoning under uncertain conditions for a wide range of applications, including disease diagnostics, genetic counseling, and emergency medical decision support system (MDSS) design.

Artificial neural networks ("ANN") are computational models inspired by an animal's central nervous system. They map inputs to outputs through a network of nodes. However, unlike BN, in ANN the nodes do not necessarily represent any actual variable. Accordingly, ANN may have a hidden layer of nodes that are not represented by a known variable to an observer.

ANNs are capable of pattern recognition and have been used for the medical and diagnostics fields. Their computing methods make it easier to understand a complex and unclear process that might go on during diagnosis of an illness based on input data a variety of input data including symptoms. While still facing steep limitations, ANN has demonstrated to be suitable in CDSS design and other biomedical applications, such as diagnosis of myocardial infarction, MDSS for leukemia management, and cancer detection.

Support vector machines ("SVM") came about from a framework utilizing of machine learning statistics and vector spaces (linear algebra concept that signifies the number of dimensions in linear space) equipped with some kind of limit-related structure. In some cases, they may determine a new coordinate system that easily separates inputs into two classifications. For example, a SVM could identify a line that separates two sets of points originating from different classifications of events.

They have been applied practically and are theoretically well-founded, but can sometimes be difficult to understand. SVMs have been applied to a number of biological domains, such as MDSS for the diagnosis of tuberculosis infection, tumor classification, and biomarker discovery.

However, there is a relatively new type of machine learning algorithm that is capable of modeling very complex relationships that have a lot of variation that are called deep neural networks. Deep neural networks have developed recently to tackle the problems of speech recognition.

In the IT industry fields, various architectures of DNN have been proposed to tackle the problems associated with algorithms such as ANN by many researchers during the last few decades. These types of DNN are CNN (Convolutional Neural Network), RBM (Restricted Boltzmann Machine), LSTM (Long Short Term Memory) etc. They are all based on the theory of ANN. They demonstrate a better performance by overcoming the back-propagation error diminishing problem associated with ANN.

Machine Learning—Training Data

Machine learning algorithms require training data to identify the features of interest that they are designed to detect. For instance, various methods may be utilized to form the machine learning models including applying randomly assigned initial weights for the network and applying gradient descent using back propagation for deep learning algorithms. In other examples, a neural network with one or two hidden layers can be used without training using this technique.

In some examples, the machine learning algorithms will be trained using labeled data, or data that represents certain features, specific actions, or characteristics, including a particular position in the mouth, a particular brush stroke, a particular user and others. In some examples, the training data will be pre-filtered or analyzed to determine certain features, including various high level filters or starting points that include motion sensing data (brush picked up, brush facing certain direction with respect to gravity). In other examples, the data will only be labeled with the outcome and the various relevant data may be input to train the machine learning algorithm.

For instance, to identify the position in the mouth, various machine learning algorithms may be utilized that input various data disclosed herein, including motion (accelerometer output, gyroscope output, magnetometer output), visual data from the camera on the base station 2, or other data that is relevant to the position of the oral hygiene device 1 during brushing. For instance, in some embodiments, the input data for determining toothbrush position may only include data output from the sensors on the oral hygiene device 1. For instance, in some examples, the input data will be labeled data from the acceleration sensor alone.

In other examples, to identify position, the input data may be various combinations of labeled data output from the accelerometer, magnetometer, and gyroscope. In some examples, the starting and ending points of the input data will be quite important. In some examples, the input data may be a combination of data output from the sensors on the oral hygiene device, and sensors on the base station 2, for example, the visual recognition or depth perception systems.

Similarly, for systems 100 that identify types of brush strokes (e.g. specific actions), the systems may utilize machine learning from combinations of data output from various sensors. In some examples, data output from the accelerometer alone may be sufficient to identify brush strokes. This is particularly the case because most brush strokes have a particular acceleration pattern that is repeated, and may include angular information with respect to gravity as disclosed herein.

In systems 100 that identify users, machine learning algorithms may be utilized to detect the face of the user, and identify the user with a unique profile. In these examples, the user may first use the system that includes a base station 2 with a camera 56 that may take an initial picture of the user. The user can then indicate their profile selection, and the system can use that picture to identify that user in the future. Over time, the system may acquire additional photos or video of the user to make the identification of the user more robust (more labeled training sets, for example).

Machine Learning—Acquisition of Training Data

In some examples, the labeling of training data may include operators that review data that is recorded while a video camera captures images of a user. In other examples, a user prompt will tell the user (1) where to brush, and (2) potentially the type of brush stroke (e.g. other specific actions) to use, to train the system. For instance, in some examples, the system 100 may utilize a coach or other instructor with a schematic of the mouth that may highlight, light up, or otherwise instruct the user where to brush. These instructions may be displayed on a display of a mobile device, for instance.

Accordingly, an automatic instruction system may be utilized to acquire training data for a particular user (to personalize the algorithm) or for many users. For instance, in the case where the system 100 implements a mobile device 30, the system may display a schematic of the user's dentition on the mobile device 30 screen, and indicate which regions the user should brush in sequence, real time. Then, the system can record the data as labeled training data, with each set of data indicating a certain position in the mouth.

Additionally, the system 100 may indicate the type of brush stroke to use, including circular, back and forth, or more complex strokes as disclosed herein. Accordingly, these will all provide input training data to the system 100 to learn how to identify positions in the mouth and certain brush strokes.

In some examples, however, the input data from the coach style acquisition may be required to be filtered, have the dimensionality reduced before feeding the labeled data into the algorithm for developing a model. For instance, a principal component analysis or other dimensionality reduction method may be implemented before the labeled data is fed into the algorithm(s).

In other examples, various filters may be utilized to filter the data before labeling and entering the data as training data. For instance, if a machine learning model for identifying position is being developed, the system may filter out various accelerations that include fast time changes, or periodic accelerations that are related to brush strokes rather than position. Similarly, for brush strokes, accelerations that are steady (e.g. gravitational) may be filtered out and only periodic accelerations will be analyzed or fed into the system. In other examples the data may not be pre-filtered and the sensitive deep learning algorithms may reliably determine position with additional data.

In other examples, the data may be pre-filtered or post-filtered (later rejected after analysis) in case the user is performing someone action wrong or not in accordance with the instructions displayed on the mobile 30 or other device display. Additionally, various filters or techniques may be utilized to determine when the user is in position and complying with the instructions, for instance once a periodic brushing is detected (with a periodic change in acceleration for example).

Presentation of Feedback

Once the system's 100 controller(s) 13, or other processors contained in the smartphone, servers, or other components of the system 100 have analyzed the usage data 78, feedback may be presented to the user 80 through the speaker 50, the visual indicators 52 on the oral hygiene device 1, or through an associated mobile device 30 or other computing device in data communication with the system 100. This feedback may be presented instantaneously or available for access to check progress.

For instance, instantaneous feedback may be provided to the user 80 during brushing, that includes indications by audio or visual means that indicate how much time is left, whether to brush harder or softer, whether certain quadrants have been sufficiently brushed, and when brushing is completed. For example, a red light or stop sound may be produced through the speaker 50 to indicate the brushing is completed.

Additionally, historic and average brushing times and positional data may be presented to the user 80 on the mobile device or other computing device using graphs, charts, percentages and other metrics. For instance, the user could be presented with the average time spent per day, per quadrant, and the average days the user brushes once, twice or other times. Additionally, the average time spent brushing per tooth may be calculated and presented to the user on the mobile device 30 or other computing device. A program 15 running on the mobile device may control the presentation of the data, using the mobile device 30 controller 13.

In some examples, the system may combine the filtered and processed position and brush stroke identifications, and potentially tarter identification to give holistic feedback. For instance, in some examples, the feedback will not only be related to the time in each position of the mouth, but will also include the strokes used in each position of the mouth. In some examples, certain stroke techniques will present higher feedback scores to the user, or certain strokes that are used in certain positions in the mouth.

Accordingly, as show in FIGS. 9A and 9B, an application according to some implementations may include a mobile device 30 display 910 that may include a heatmap 920 or other visual representation of the positions the user has brushed, the accuracy of the brushing in each position, and the amount of time, and the type of stroke used. This information can provide a user with multiple goals for improving brushing.

Referring to FIG. 10, an oral hygiene system 1000 includes an oral hygiene device 1002, a sensor 1004, a display device 1006, a processor 1008, a memory device 1010, and a communication module 1012. The oral hygiene system 1000 is generally used to promote compliance with an oral hygiene regimen by executing an associated application using the processor 1008 and memory device 1010, and displaying the application on the display device 1006.

The oral hygiene device 1002 is the same as or similar to the oral hygiene device 1 (FIG. 3A) described above, and more generally can be any typical manual toothbrush or electric toothbrush. The oral hygiene device 1002 includes a head 1002*a* and a handle 1002*b* (FIG. 13B). The sensor 1004 is generally used to track motion of the oral hygiene device 1002. The sensor 1004 can be an optical sensor, a camera, a pressure sensor, a motion sensor, a proximity sensor, a depth perception sensor, a gyrometer, a magnetometer sensor, any other suitable sensor, or any combination thereof.

The display device 1006 is generally used to display still images, video images, or both. The display device 1006 can be, for example, the display device a smartphone, a tablet, a laptop, a smart watch, a television, a smart mirror, or any other suitable display device. The display device 1006 can also include a user interface to receive inputs from a user, such as, for example, a touchscreen interface, a graphical user interface, a hardware interface, or the like, or any combination thereof.

The memory device 1010 stores instructions (e.g., an associated software application) that are executable by the processor 1008. The sensor 1004, the display device 1006, the processor 1008, and the memory device 1010 are communicatively coupled to one another. While the sensor 1004, the processor 1008, the memory device 1010, and the display device 1006 are shown as separate components, the sensor 1004, the processor 1008, the memory device 1010, or any combination thereof, can be included in a single housing (e.g., within a smartphone). Alternatively, the processor 1008 and the memory device 1010 can be included in a controller (not shown) that is the same as or similar to the controller 13 described above.

In some implementations, the sensor 1004, the display device 1006, the processor 1008, the memory 1010, and the communication module 1012 can be integrated into a single housing 1014. In some implementations, the housing 1014 is a smartphone. The smartphone can further include a speaker (not shown), a light (e.g., an LED light), a camera (e.g., a front-facing camera), a microphone, or the like, or any combination thereof. Alternatively, the sensor 1004, the display device 1006, the processor 1008, the memory 1010, the communication module 1012, or any combination thereof can be decoupled from one another as separate components. For example, the housing 1014 can include the display device 1006, the memory 1008, the processor 1010, and the communication module 1012, while the sensor 1004 is a separate component (e.g., a standalone sensor that is part of a base station for the oral hygiene device 1002). Thus, various combinations of the basic components described herein can be integrated into the housing 1014.

Referring to FIGS. 11A and 11B, a schematic 1100 and a timer 1102 are displayed on the display device 1006. Typically, the processor 1008 executes an associated software application to cause the schematic 1100 and timer 1102 to be displayed on the display device 1006.

The schematic 1102 represents at least a portion of a set of teeth of a user. As shown, the schematic 1102 includes a set of maxillary teeth 1110 and a set of mandibular teeth 1120. The set of maxillary teeth 1110 is divided into a plurality of maxillary sections 1112, and the set of mandibular teeth 1120 is also divided into a plurality of mandibular sections 1122. As shown, the plurality of maxillary sections 1112 and the plurality of mandibular sections 1122 each include four sections having substantially the same size. Each of the plurality of maxillary sections 1112 includes an occlusal surface 1114, an inner surface 1116, and an outer surface 1118. Similarly, each of the plurality of mandibular sections 1122 includes an occlusal surface 1124, an inner surface 1126, and an outer surface 1128.

In some implementations, the plurality of maxillary sections 1112 and/or the plurality of mandibular sections 1122 can further include representations of individual teeth (not shown). While the schematic 1102 is shown as including plan views of the set of maxillary teeth 1110 and the set of mandibular teeth 1120, other views and orientations of the set of teeth are contemplated. For example, the schematic 1100 can include front or side views of maxillary teeth, mandibular teeth, or both. Further, in some implementations, the schematic 1012 includes only a portion of the set of teeth of the user. For example, the schematic 1100 can include only the set of maxillary teeth 1110, the set of mandibular teeth 1120, or any number of the plurality of maxillary sections 1112 or mandibular sections 1122 (e.g., one section, three sections, etc.), or any combination thereof. Further still, while the schematic 1100 is shown as two-dimensional, the schematic 1102 can be a three-dimensional representation of a set of teeth of a user. In other implementations, the schematic 1100 can further include a representation of a tongue of the user (not shown).

Referring to FIG. 11B, a first indicium 1131, a second indicium 1132, and a third indicium 1133 are displayed on the display device 1006 and overlaid on the schematic 1100. Generally, the indicium 1131, 1132, 1133 are overlaid on the schematic 1100 to promote the user of the system 1000 to brush an associated section of the user's teeth. As shown, the first indicium 1131 is overlaid on a second section of the plurality of mandibular sections 1122. Overlaying the first indicium 1131 as shown associates the first indicium 1131 with the second section of the plurality of mandibular sections 1122. The second indicium 1132 is overlaid on a fourth section of the plurality of mandibular sections 1122 to associate the second indicium 1132 with the fourth section of the plurality of mandibular sections 1122. Similarly, the third indicium 1133 is overlaid on a second section of the plurality of maxillary sections 1112 to associate the third indicium 1133 with the second section of the plurality of maxillary sections 1112. In this manner, various indicia can be overlaid on the schematic 1100 to associate each indicium with a desired portion of the set of teeth in the schematic 1100.

The position of each of the indicium 1131, 1132, 1133 relative to the schematic 1100 can be used to further associate each indicium with a particular surface of the set of teeth. For example, as shown, the first indicium 1131 is overlaid directly on top of the second section of the plurality of mandibular sections 1122. Thus, the first indicium 1131 is associated with the occlusal surface 1124 of the second section of the plurality of mandibular sections 1122. The second indicium 1132 is overlaid on the schematic 1110 such that the second indicium 1132 is generally adjacent to, but spaced from, the fourth section of the plurality of mandibular sections 1122. This positioning of the second indicium 1132 associates the second indicium with the inner surface 1126 of the fourth section of the plurality of mandibular sections 1122. The third indicium 1133 is overlaid on the schematic 1100 such that it partially overlaps the second section of the plurality of maxillary sections 1112, associating the third indicium 1133 with both the occlusal surface 1114 and the outer surface 1118. In this manner, the positioning of each indicium can be used to associate the indicium with various sections of the schematic 1100 with increasing granularity. While not shown, an indicium can also be associated with a plurality of sections by being overlaid on the schematic 1100 such that it overlaps plurality of sections of the maxillary or mandibular sections of teeth.

Each of the indicium 1131, 1132, 1133 can be a still image, a video image, an animated image, or the like. The image(s) chosen for each indicium are generally used to promote a user of the system 1000 to brush the associated section of the user's teeth. To that end, the images can have a negative connotation which encourages the user to desire to remove the image from the display device. For example, the indicia can be an image of a monster, an alien, a frowning face, a fictional villain/character, a storm cloud, or the like, or any combination thereof. Alternatively, the image(s) can be associated with a positive connotation which encourages the user to attempt to collect or acquire the item/thing in the image. For example, the indicia can be images of coins or money, points, stars, animals, collectibles, or the like, or any combination thereof. Finally, the indicia can more generally by any image, such as a shape (e.g., a circle, a square, a triangle, or any other polygon), a checkmark, other symbol, or any combination thereof.

While the schematic 1100 is shown as including three indicia (indicium 1131, 1132, and 1133), any number of indicium are possible, such as, for example, one indicium, two indicium, five indicium, ten indicium, sixteen indicium, etc.

Figure 12:
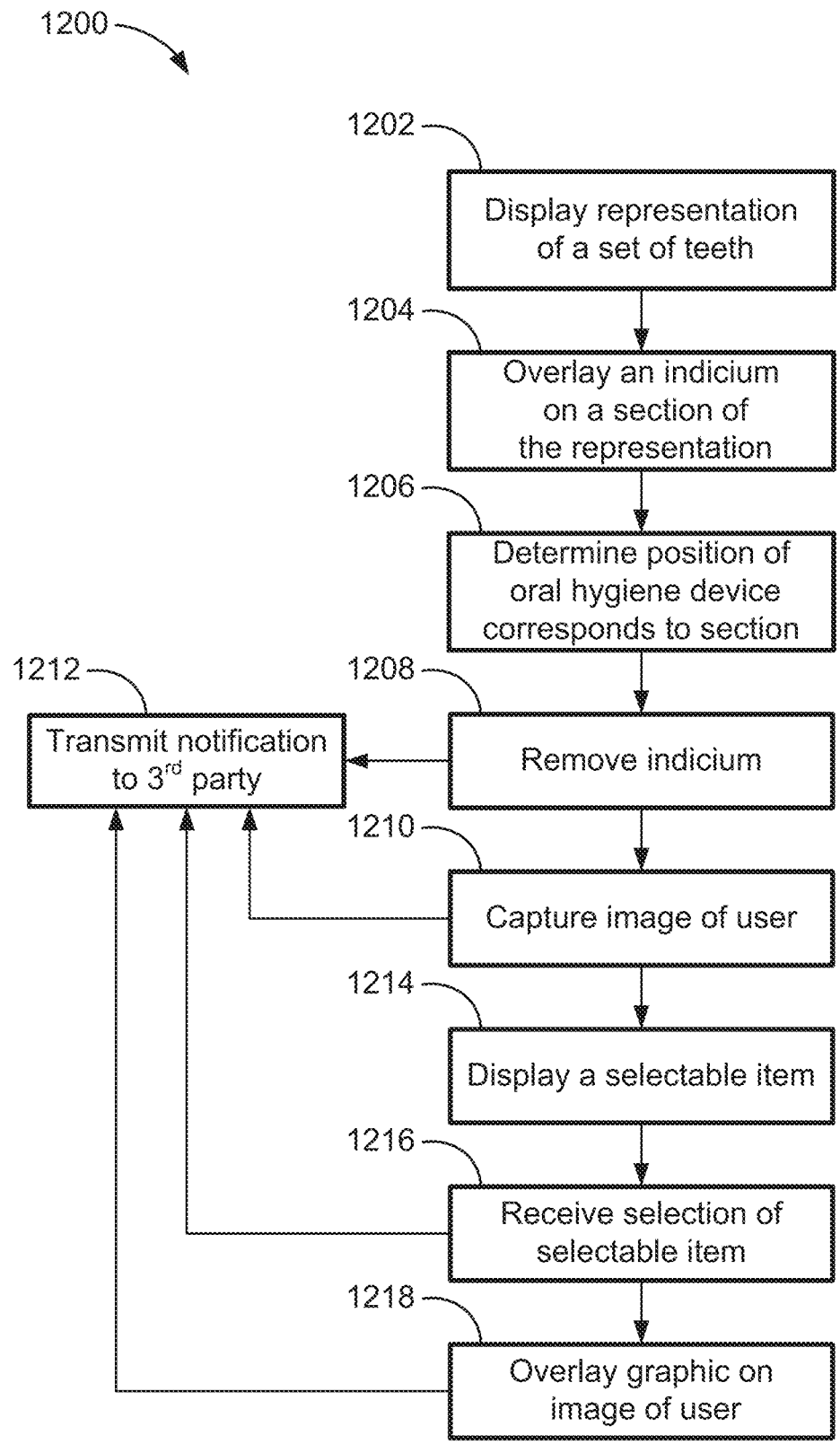
FIG. 12 is a schematic illustration of a method for operating the oral hygiene system of FIG. 10.

Referring to FIG. 12, a method 1200 for promoting compliance with an oral hygiene regimen using the system 1000 includes a first step 1202, a second step 1204, a third step 1206, a fourth step 1208, and a fifth step 1210.

The first step 1202 includes displaying the schematic 1100 on the display device 1106 (FIG. 11A). The first step 1202 can be initiated by a variety of triggering events, such as, for example, initiation of a user brushing session. The user can indicate that a user brushing session has been initiated by providing an input (e.g., pressing a button on the display device 1006). Alternatively, the first step 1202 can be initiated by determining, using the sensor 1004, that the oral hygiene device 1002 is moving (e.g., a user has picked up the toothbrush). This movement indicates that the user has initiated a user brushing session and initiates the first step 1202 of the method 1200.

The second step 1204 includes overlaying an indicium on the schematic 1100 displayed on the display device 1006. For example, the first indicium 1131 (FIG. 11B) can be overlaid on the second section of the plurality of mandibular sections 1122. The first indicium 1131 can be overlaid on the schematic 1100 in a variety of ways. For example, the first indicium 1131 can abruptly appear on the schematic 1100, or the indicium 1131 can slowly appear (e.g., the indicium 1131 initially appears semi-transparent and becomes less transparent) over a predetermined period of time (e.g., one second, five seconds, ten seconds, etc.). In some implementations, the first indicium 1131 can be overlaid during the second step 1204 using an animation. For example, the first indicium 1131 may first appear on the far left side of the display device 1006 and move towards its final position on the schematic 1100. Overlaying the first indicium 1131 during the second step 1204 can also include an associated sound that is played through a speaker (not shown).

Like the first step 1202, the second step 1204 can be initiated by a variety of triggering events. For example, the second step 1204 can be initiated after the system 1000 has determined that a predetermined amount of time has elapsed since a user brushing session has been initiated (e.g., two seconds, ten seconds, thirty seconds, one minute, etc.). The second step 1204 can also be initiated automatically upon initiation of a user brushing session such that the overlaid indicium is displayed at the same time that the schematic 1100 is displayed on the display device 1006 during the first step 1202. Alternatively, the triggering event for initiating the second step 1204 can be a user input received by the display device 1006.

The indicium can be overlaid on any portion of the schematic 1100 during the second step 1204 (e.g., the first indicium 1131, the second indicium 1132, or the third indicium 1133). Further, the second step 1204 can include overlaying a plurality of indicium (e.g., the first indicium 1131 and the third indicium 1133). The section of the schematic 1100 chosen for overlaying the indicium during the second step 1204 can be random or predetermined. For example, an individual (e.g., the user, a parent of the user, a dentist, or any other third party) can input, via the display device 1006, the section(s) of the schematic 1100 where an indicium should be overlaid. For example, if the user has had a cavity or other dental problems in a certain area of the user's mouth, the indicium can be overlaid on the corresponding section of the schematic 1100 during the second step 1204 to aid in preventing future cavities or dental problems in that area.

The third step 1206 includes determining a position of the oral hygiene device 1002 relative to the mouth/teeth of the user. Generally, the system 1000 determines the position of the oral hygiene device 1002 in the user's mouth using the sensor 1004, the processor 1008, and the memory device 1010. Any of the mechanisms described above can be used to determine the position of the oral hygiene device 1002 during the third step 1206 (e.g., a visual pattern, an optical sensor, a motion sensor, a proximity sensor, a pressure sensor, a depth perception sensor, a camera, a gyrometer, a magnetic field generator and magnetometer sensor, or any combination thereof).

During the third step 1206, the position of the oral hygiene device 1002 is associated with a section of the set of teeth of the user. This section of the set of teeth of the user is then associated with a section of the schematic 1100 (FIGS. 11A & 11B). For example, if it is determined that the head of the oral hygiene device 1002 is positioned on an outer surface of a front left quadrant of the user's mandibular teeth (e.g., an upper lateral incisor), the position of the head of the oral hygiene device 1002 is associated with the outer surface 1128 of the second section of the plurality of mandibular sections 1122 in the schematic 1100. If the oral hygiene device 1002 is positioned generally adjacent to or near the mouth of the user, but is not directly adjacent to any teeth, the position is not associated with a section of the schematic 1100.

The fourth step 1208 includes removing the indicium from the display device 1006 responsive to determining that the head of the oral hygiene device 1002 is positioned directly adjacent to (e.g., contacting) a section of the set of teeth that corresponds to the section of the schematic 1100 including the indicium for a predetermined amount of time. For example, as described above, the first indicium 1131 is overlaid on the occlusal surface 1124 of the second section of the plurality of mandibular sections 1122, and that section of the schematic 1100 is associated with a section of the set of teeth of the user. If it is determined that the head of the oral hygiene device 1002 is positioned on the associated section of the set of teeth for a predetermined period of time, the first indicium 1131 is removed from the display device 1006.

The predetermined amount of time for removing an indicium is typically selected to prompt the user to brush the associated section of the set of teeth for a certain period of time in accordance with proper brushing habits, and more generally can be any period of time (e.g., one second, five seconds, ten seconds, one minute, two minutes, etc.). The timer 1102 (FIGS. 11A and 11B) can be used either to show the user how long they have brushed a particular section of the set of teeth, as a countdown to show a user how much longer they need to brush an associated section of the set of teeth to remove the indicium, to show the user the total time that has elapsed in a given user brushing session, or any combination thereof.

Requiring the user to brush the associated section of the set of teeth for the predetermined period of time to remove an indicium aids in promoting compliance with a proper oral hygiene regimen. For example, if the predetermined period of time is five seconds, the user must brush the occlusal surface of the front left quadrant of the user's teeth for five seconds in order to remove the first indicium 1131 from the display device 1106. In this example, the first indicium 1131 can be an image of a monster, which can incentivize or encourage a user to brush the associated section of their teeth to remove the image of the monster.

Removing the indicium during the fourth step 1208 can be accomplished in a number of ways. For example, in response to the conditions for removal described above, the first indicium 1131 can be immediately removed from the display device 1006. Alternatively, the transparency of the first indicium 1131 can be increased during the predetermined amount of time such that the first indicium slowly disappears from the display device 1006. In another example, removal of the first indicium 1131 includes an animation (e.g., the first indicium 1131 moves across the display device 1006 and disappears).

In some implementations, the fourth step 1208 further includes overlaying a removal image on the indicium prior to removing the indicium from the display device 1006. The removal image is generally used to emphasize that the indicium is being removed from the display device. For example, the removal image can be an "X", a lightning bolt, a cloud, a fire/explosion, or any other image conveying to the user that the indicium is being removed. In one example, the first indicium 1131 is an image of a monster and the removal image is an image of a lightning bolt, which permits a user to perceive that the monster has been "destroyed". More generally, the removal image can be any still image or video image.

The fourth step 1208 can also include determining that movement of the head of the oral hygiene device 1002 corresponds to a predetermined brush stroke type (e.g., the circular brush stroke, the back-and-forth brush stroke, or the angled brush stroke described herein). In such implementations, the indicium is removed after determining (1) the position of the head of the oral hygiene device 1002 corresponds to the section of the schematic 1100 associated with the indicium for a predetermined amount of time, and (2) movement of the head of the oral hygiene device 1002 corresponds to a predetermined brush stroke during at least a portion of the predetermined amount of time. More generally, any other triggering event or condition can be added to the fourth step 1208 prior to causing the indicium to be removed from the display device 1006.

The second step 1204, the third step 1206, and the fourth step 1208 can be repeated one or more times to further aid in promoting compliance with an oral hygiene regimen. For example, after the first indicium 1131 (FIG. 11B) is removed during the fourth step 1208, the second step 1204 is repeated and the second indicium 1132 (FIG. 11B) is overlaid on the schematic 1100. The third step 1206 is then repeated to again determine the position of the oral hygiene device 1002, and the second indicium 1132 is removed in the fourth step 1208 once the conditions described above are satisfied. In this manner, a plurality of indicium can be overlaid and removed during a given brushing session to promote compliance with an oral hygiene regimen. The indicia can be overlaid on the schematic 1100 during the repeating of the steps 1204, 1206, and 1208 in a predetermined sequence or a random sequence. For example, a first predetermined sequence can include sequentially overlaying an indicium/indicia on each section of the schematic 1100 to urge the user to brush all of the corresponding sections of the user's teeth (e.g., the indicia appear left to right along the plurality of maxillary sections 1112 in FIG. 11A as steps 1204, 1206, and 1208 are repeated). In another example, a second predetermined sequence can include sequentially overlaying indicia in accordance with the user's brushing history, which can be stored in the memory device 1010 (e.g., overlaying an indicium on a section of the schematic 1100 that the user most often misses while brushing, or a section in which the user has had a cavity).

In some implementations, the fourth step 1208 does not remove the indicium completely from the display device 1006 but instead moves the indicium from a first location on the schematic 1100 to a second position on the schematic 1100. For example, rather than removing the first indicium 1131 from the schematic 1100 after all of the conditions are satisfied, the first indicium 1131 can be moved to a second position on the schematic (e.g., the position of the second indicium 1132 shown in FIG. 11B).

The fifth step 1210 includes capturing an image of the user using a camera. As described above, the display device 1006 can include a camera, the sensor 1004 can include a camera, or the camera can be a separate component. The image of the user can include an augmented reality image that is overlaid on at least a portion of the image of the user. For example, the augmented reality image can be a hat, ears, eyes, a nose, clothing, sparkles, or other objects or graphics that are superimposed on the image of the user. Further, the image can include an associated customized message that the user can input using a user input of the display device 1006 (e.g., a touchscreen keyboard).

The sixth step 1212 includes transmitting a notification to a third party (e.g., the user's parents or dentist) via the communication module 1012. The notification can include the image of the user and/or augmented reality image taken during the fifth step 1210. The notification can also include information regarding the user brushing session (e.g., how long the user has brushed teeth, if the user successfully removed all indicia, etc.). The notification further aids in promoting compliance with an oral hygiene routine by allowing a third party to monitor the user's brushing habits. The notification can also be sent to a user social media account (e.g., Facebook, Twitter, etc.) to be shared with third parties. While the sixth step 1212 is shown as being subsequent to the fifth step 1210, the sixth step 1212 can also be directly subsequent to completion of the fourth step 1208 (i.e., the notification is transmitted without capturing an image of the user).

The seventh step 1214 includes displaying a selectable item on the display device 1006. Referring to FIG. 13A, a plurality of selectable items 1300 are displayed on the display device 1006. The plurality of selectable items 1300 are generally used as a user interface to permit the user to control or initiate various aspects of the associated application. For example, selecting one of the plurality of selectable items 1300 can cause the camera described above to take a photo of the user (e.g., initiate the fifth step 1210).

While the plurality of selectable items 1300 is shown as included two selectable items, any number of selectable items can be displayed on the display device 1006 (e.g., one selectable item, five selectable items, fifteen selectable items, etc.). While shown as rectangular in FIG. 13A for illustrative purposes, the plurality of selectable items 1300 generally can be text, images, symbols, or combinations thereof.

In some implementations, the number of the plurality of selectable items 1300 can correspond the number of indicium that are removed from the display device 1006 as steps 1202 through 1208 are repeated during a brushing session. For example, if the user removes two indicia from the display device 1006 during a brushing session, the plurality of selectable items 1300 includes two selectable items that the user can select. Similarly, the number of the plurality of selectable items 1300 can increase as the user successfully removes indicia during the course of a plurality of brushing sessions. For example, a given selectable item will only appear (or be "unlocked") after the user has removed all of the indicia during a predetermined number of consecutive brushing sessions (e.g., two sessions, four sessions, ten sessions, etc.). In this manner, the number of the plurality of selectable items 1300 can be used as a rewards system to incentivize or encourage the user to comply with a proper oral hygiene regimen.

As shown in FIG. 13A, the plurality of selectable items 1300 are displayed on the display device 1006 within a coordinate system 1302. Each of the plurality of selectable items 1300 is associated with a position within coordinate system 1302. As shown, a first one of the plurality of selectable items 1300 has a position 1304 within the coordinate system 1302.

The eighth step 1216 (FIG. 12) includes receiving a selection of a selectable item displayed on the display device 1006. The user selects one or more of the plurality of selectable items 1300 by moving the oral hygiene device 1002 relative to the display device 1006 to a position that corresponds with the position of the selectable item within the coordinate system 1302.

Referring to FIG. 13B, the oral hygiene device 1002 is positioned in a three-dimensional volumetric space 1320 that is generally in front of the display device 1006 and/or the sensor 1004. As described above, the sensor 1004 and display device 1006 can be included in a housing (e.g., a smartphone). Preferably, the sensor 1004 is a camera that is included with the display device 1006 as part of a smartphone such that the three-dimensional volumetric space 1320 is generally in front of both the display device 1006 and the sensor 1004. In such implementations, the three-dimensional volumetric space 1320 corresponds to the field of view of the sensor 1004.

As shown, the three-dimensional volumetric space 1320 includes a coordinate system 1322. The coordinate system 1322 permits the system 1000 to determine, using the sensor 1004, the processor 1008, and the memory device 1010, a position of the head 1002*a* of the oral hygiene device 1002 within the three-dimensional volumetric space 1320. The coordinate system 1322 of the three-dimensional volumetric space 1320 corresponds to the coordinate system 1302 of the display device 1006, meaning that a given position within the coordinate system 1302 (FIG. 13A) has an associated position within the coordinate system 1322 (FIG. 13B).

To select one of the plurality of selectable items 1300 (FIG. 13A), the user moves the oral hygiene device 1002 within three-dimensional volumetric space 1320 until the position of the head 1002*a* is the position within the coordinate system 1322 (FIG. 13B) that corresponds to the position of the selectable item within the coordinate system 1302 (FIG. 13A). In addition, rather than requiring the position of the head 1002*a* within the coordinate system 1322 to exactly correspond to the position of the selectable item in the coordinate system 1302, a selection may be received by determining that the position of the head 1002*a* within the coordinate system 1322 is within a predetermined distance of the position in the coordinate system 1322 that corresponds with the position of the selectable item in the coordinate system 1302 (FIG. 13A). In other words, the head 1002*a* does not need to be exactly positioned to select a selectable item. The predetermined distance can be, for example, a quarter inch, one inch, two inches, four inches, six inches, or any other suitable distance. After the user moves the head 1002*a* of the oral hygiene device 1002 to the associated position, the system 1000 receives a selection of that selectable item, which triggers the corresponding function (e.g., causes the camera to take a photo of the user, to cause an augmented reality image to be overlaid on an image of the user, etc.).

While the system 1000 and associated method 2000 have been shown and described herein as displaying the schematic 1100, the timer 1102, and/or the plurality of selectable items 1300, it is expressly contemplated that other images can be displayed on the display device 1006. For example, in some implementations, a representation of the oral hygiene device 1002 can be displayed on the display device 1002. The representation of the oral hygiene device can be animated such that its movement is substantially similar to the movement of the oral hygiene device 1002 (e.g., if the user is moving the oral hygiene device 1002 side-to-side, the representation also moves side-to-side). Further, the representation of the oral hygiene device can be an image of an oral hygiene device (e.g., an image of a typical toothbrush or an image of the actual oral hygiene device 1002), or more generally any other image. For example, the representation of the oral hygiene device can be a sword, a baseball bat, a hockey stick, or any other object. Thus, the user can move the oral hygiene device 1002 to cause a corresponding movement of the representation of the oral hygiene device on the display device 1006.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Those skilled in the art will recognize that many changes may be made to the described embodiments without departing from the spirit and scope of the invention. Furthermore, those skilled in the art will also recognize that certain embodiments described for one device or system can be readily, or with slight modification, be included in the embodiments described for another device or system, without departing from the spirit and scope of the invention.

By way of example, the following selected embodiments are illustrative examples of the present disclosure.

SELECTED EMBODIMENTS

Although the above description and the attached claims disclose a number of embodiments, other alternative aspects of the invention are disclosed in the following further embodiments.

Embodiment 1. A method for promoting compliance with an oral hygiene regimen, the method comprising: displaying, on a display device, a representation of at least a portion of a set of teeth of a user; overlaying an indicium on the representation such that the indicium is associated with a first section of the representation; and responsive to a determination, via at least one of one or more processors, that a head of an oral hygiene device is positioned directly adjacent to a first section of the set of teeth that corresponds to the first section of the representation for at least a predetermined amount of time, causing the indicium to be removed from the display device.

Embodiment 2. The method according to any one of embodiment 1, further comprising, responsive to the removing the indicium, transmitting a notification to a third party via a communication module.

Embodiment 3. The method according to any one of embodiments 1 and 2, further comprising capturing an image of the user using a camera and displaying the image of the user on the display device.

Embodiment 4. The method according to any one of embodiments 1-3, further comprising displaying a selectable item on the display device, the selectable item being positioned at a first location within a coordinate system, the first location within the coordinate system being associated with a location in a volumetric space generally in front of the display device; and responsive to a determination, via at least one of the one or more processors, that the head of the oral hygiene device is positioned within a predetermined distance of the location in the volumetric space associated with the first location in the coordinate system for a predetermined amount of time, receiving a selection of the selectable item.

Embodiment 5. The method according to any one of embodiment 4, further comprising capturing an image of the user using a camera and displaying the image of the user on the display device, and subsequent to receiving the selection of the selectable item, transmitting the image of the user to a third party via a communication module.

Embodiment 6. The method according to any one of embodiment 4, further comprising, capturing an image of the user using a camera and displaying the image of the user on the display device, and subsequent to receiving the selection of the selectable item, overlaying a graphic associated with the selectable item on the image of the user on the display device.

Embodiment 7. The method according to any one of embodiments 1-6, further comprising transmitting the image of the user and the overlaid graphic to a third party via a communication module.

Embodiment 8. The method according to any one of embodiments 1-7, wherein the determination further includes determining that movement of the head of the oral hygiene device corresponds to a predetermined brush stroke type.

Embodiment 9. The method according to any one of embodiment 8, wherein the predetermined brush stroke type is a circular brush stroke, a back-and-forth brush stroke, an angled brush stroke, or any combination thereof.

Embodiment 10. The method according to any one of embodiments 1-9, wherein the first teeth section representation corresponds to a complete set of maxillary teeth or a complete set of mandibular teeth.

Embodiment 11. The method according to any one of embodiments 1-10, wherein the first section of the representation corresponds to one of a plurality of sections of a complete set of maxillary teeth or one of a plurality of sections of a complete set of mandibular teeth.

Embodiment 12. The method according to any one of embodiments 1-11, wherein the first section of the set of teeth has an inner surface, an outer surface, and an occlusal surface, wherein the determining further includes determining that the head of the oral hygiene device is directly adjacent to one of the inner surface, the outer surface, or the occlusal surface of the set of teeth.

Embodiment 13. An oral hygiene system, the system comprising: an oral hygiene device including a handle and a head; a sensor; a display device; one or more processors; and a memory device storing instructions that, when executed by at least one of the one or more processors cause the oral hygiene system to, display, on the display device, a representation of at least a portion of a set of teeth of a user; overlay an indicium on the representation such that the indicium is associated with a first section of the representation; responsive to a determination, via at least one of the one or more processors, that the head of the oral hygiene device is positioned directly adjacent to a first section of the set of teeth that corresponds to the first section of the representation for at least a predetermined amount of time, causing the indicium to be removed from the display.

Embodiment 14. The system according to any one of embodiment 13, further comprising a communication module that is configured to transmit a notification to a third party responsive to removal of the indicium from the display device.

Embodiment 15. The system according to any one of embodiments 13 and 14, further comprising a camera configured to capture an image of a user, wherein the instructions, when executed by at least one of the one or more processors cause the display device to display the image of the user.

Embodiment 16. The system according to any one of embodiment 15, further comprising a communication module that is configured to transmit the image of the user to a third party.

Embodiment 17. The system according to any one of embodiments 13-16, wherein the instructions, when executed by at least one of the one or more processors cause the oral hygiene system to display a selectable item on the display device, the selectable item being positioned at a first location within a coordinate system, the first location within the coordinate system being associated with a location in a volumetric space generally in front of the display device; and responsive to a determination, via the sensor, that the head of the oral hygiene device is positioned within a predetermined distance of the location in the volumetric space associated with the first location in the coordinate system for a predetermined amount of time, receive a selection of the selectable item.

Embodiment 18. The system according to any one of embodiment 17, wherein the instructions, when executed by at least one of the one or more processors cause the oral hygiene system to overlay a graphic associated with the selectable item on the image of the user on the display device responsive to receiving the selection of the selectable item.

Embodiment 19. The system according to any one of embodiment 18, further comprising a communication module that is configured to transmit the image of the user and the overlaid graphic to a third party.

Embodiment 20. The system according to any one of embodiments 13-19, wherein the determination further includes determining that movement of the head of the oral hygiene device corresponds to a predetermined brush stroke type.

Embodiment 21. The system according to any one of embodiment 20, wherein the predetermined brush stroke type is a circular brush stroke, a back-and-forth brush stroke, an angled brush stroke, or any combination thereof.

Embodiment 22. The system according to any one of embodiments 13-21, wherein the first section of the representation corresponds to a complete set of maxillary teeth or a complete set of mandibular teeth.

Embodiment 23. The system according to any one of embodiments 13-22, wherein the first section of the representation corresponds to one of a plurality of sections of a complete set of maxillary teeth or one of a plurality of sections of a complete set of mandibular teeth.

Embodiment 24. The system according to any one of embodiments 13-23, wherein the sensor is an optical sensor, a motion sensor, a gyrometer, a magnetometer, an accelerometer, a camera, or any combination thereof.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed:

1. A method for promoting compliance with an oral hygiene regimen, the method comprising:
displaying, on a display device, a representation of at least a portion of a set of teeth of a user;
overlaying an indicium on the representation such that the indicium is associated with a first section of the representation; and
responsive to a determination, via at least one of one or more processors, that a head of an oral hygiene device is positioned directly adjacent to a first section of the set of teeth that corresponds to the first section of the representation for at least a period of time, causing the indicium to be removed from the display device;
wherein the step of causing the indicium to be removed comprises displaying a removal image, the removal image displayed subsequent to positioning the head of the oral hygiene device adjacent the first section of the set of teeth and removed substantially simultaneously with the removal of the indicium.

2. The method of claim 1, wherein the indicium is a graphic symbol representing an object.

3. The method of claim 1, wherein the removal image is one of an "X", a lightning bolt, a cloud, or a fire/explosion.

4. The method of claim 1, further comprising displaying a selectable item on the display device, the selectable item being positioned at a first location within a coordinate system, the first location within the coordinate system being associated with a location in a volumetric space generally in front of the display device; and responsive to a determination, via at least one of the one or more processors, that the head of the oral hygiene device is positioned within a predetermined distance of the location in the volumetric space associated with the first location in the coordinate system for an amount of time, receiving a selection of the selectable item.

5. The method of claim 4, further comprising capturing an image of the user using a camera and displaying the image of the user on the display device, and subsequent to receiving the selection of the selectable item, transmitting the image of the user to a third party via a communication module.

6. The method of claim 4, further comprising, capturing an image of the user using a camera and displaying the image of the user on the display device, subsequent to receiving the selection of the selectable item, overlaying a graphic associated with the selectable item on the image of the user on the display device, and transmitting the image of the user and the overlaid graphic to a third party via a communication module.

7. The method of claim 1, wherein the indicium is an image of a monster, an alien, a frowning face, a fictional character, a storm cloud, coins, money, points, stars, animals, collectibles, a circle, a square, a triangle, or a checkmark.

8. The method of claim 1, wherein the determination further includes determining that movement of the head of the oral hygiene device corresponds to a predetermined brush stroke type selected from a plurality of predetermined brush stroke types.

9. The method of claim 8, wherein the plurality of predetermined brush stroke type is one of a circular brush stroke, a back-and-forth brush stroke, an angled brush stroke, or any combination thereof.

10. The method of claim 1, wherein the first teeth section representation corresponds to a complete set of maxillary teeth or a complete set of mandibular teeth.

11. The method of claim 1, wherein the first section of the representation corresponds to one of a plurality of sections of a complete set of maxillary teeth or one of a plurality of sections of a complete set of mandibular teeth.

12. The method of claim 1, wherein the first section of the set of teeth has an inner surface, an outer surface, and an occlusal surface, wherein the determining further includes determining that the head of the oral hygiene device is directly adjacent to one of the inner surface, the outer surface, or the occlusal surface of the set of teeth.

13. An oral hygiene system, the system comprising:
an oral hygiene device including a handle and a head;
a sensor;
a display device;
one or more processors; and
a memory device storing instructions that, when executed by at least one of the one or more processors cause the oral hygiene system to,
display, on the display device, a representation of at least a portion of a set of teeth of a user;
overlay an indicium on the representation such that the indicium is associated with a first section of the representation;
responsive to a determination, via at least one of the one or more processors, that the head of the oral hygiene device is positioned directly adjacent to a first section of the set of teeth that corresponds to the first section of the representation for at least a period of time, causing the indicium to be removed from the display;
wherein causing the indicium to be removed comprises displaying a removal image, the removal image displayed subsequent to positioning the head of the oral hygiene device adjacent the first section of the set of teeth and removed substantially simultaneously with the removal of the indicium.

14. The system of claim 13, further comprising a communication module that is configured to transmit a notification to a third party responsive to removal of the indicium from the display device.

15. The system of claim 13, further comprising a camera configured to capture an image of a user, wherein the instructions, when executed by at least one of the one or more processors cause the display device to display the image of the user.

16. The system of claim 15, further comprising a communication module that is configured to transmit the image of the user to a third party.

17. The system of claim 13, wherein the instructions, when executed by at least one of the one or more processors cause the oral hygiene system to display a selectable item on the display device, the selectable item being positioned at a first location within a coordinate system, the first location within the coordinate system being associated with a location in a volumetric space generally in front of the display device; responsive to a determination, via the sensor, that the head of the oral hygiene device is positioned within a predetermined distance of the location in the volumetric space associated with the first location in the coordinate system for a predetermined amount of time, receive a selection of the selectable item; and wherein the instructions, when executed by at least one of the one or more processors, cause the oral hygiene system to overlay a graphic associated with the selectable item on the image of the user on the display device responsive to receiving the selection of the selectable item.

18. The system of claim 13, wherein the indicium is one of a still image, a video image, or an animated image.

19. The system of claim 13, wherein the removal image is one of an "X", a lightning bolt, a cloud, or a fire/explosion.

20. The system of claim 13, wherein the indicium is an image of a monster, an alien, a frowning face, a fictional character, a storm cloud, coins, money, points, stars, animals, collectibles, a circle, a square, a triangle, or a checkmark.

* * * * *